(12) United States Patent
Nagatomi et al.

(10) Patent No.: US 9,377,408 B2
(45) Date of Patent: Jun. 28, 2016

(54) SAMPLE-HOLDING CARRIER AND FLUORESCENCE DETECTION DEVICE USING SAME

(71) Applicant: Panasonic Intellectual Property Management Co., Ltd., Osaka (JP)

(72) Inventors: Kenji Nagatomi, Osaka (JP); Morio Nakatani, Osaka (JP); Masaya Nakatani, Osaka (JP); Akio Oki, Osaka (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 0 days.

(21) Appl. No.: 14/726,157

(22) Filed: May 29, 2015

(65) Prior Publication Data

US 2015/0276606 A1      Oct. 1, 2015

Related U.S. Application Data

(63) Continuation of application No. PCT/JP2013/006387, filed on Oct. 29, 2013.

(30) Foreign Application Priority Data

Nov. 30, 2012 (JP) ................. 2012-263601

(51) Int. Cl.
*G01N 21/64* (2006.01)
*B01L 3/00* (2006.01)
(Continued)

(52) U.S. Cl.
CPC .......... *G01N 21/6486* (2013.01); *B01L 3/5085* (2013.01); *B01L 3/502761* (2013.01); *G01N 21/03* (2013.01); *G01N 21/07* (2013.01); *G01N 21/6452* (2013.01); *G01N 21/69* (2013.01); *B01L 2200/0668* (2013.01); *B01L 2300/0645* (2013.01); *B01L 2300/0806* (2013.01);
(Continued)

(58) Field of Classification Search
None
See application file for complete search history.

(56) References Cited

U.S. PATENT DOCUMENTS

2005/0255474 A1* 11/2005 Fujita ................. G01N 21/6428
435/6.12
2006/0275181 A1    12/2006 Takeda et al.
(Continued)

FOREIGN PATENT DOCUMENTS

EP        1724018 A2    11/2006
JP        10-078393 A    3/1998
(Continued)

OTHER PUBLICATIONS

International Search Report dated Feb. 4, 2014 issued in International Patent Application No. PCT/JP2013/006387 (English translation).
(Continued)

*Primary Examiner* — Casey Bryant
(74) *Attorney, Agent, or Firm* — McDermott Will & Emery LLP

(57) ABSTRACT

A sample holding carrier includes: a substrate to which irradiation light is entered from an under face; a first reflective film disposed on a top face side of the substrate and having electrical conductivity; a sample accommodating portion disposed on a top face side of the first reflective film and having a bottom portion; and a first current carrying part configured to apply a voltage to the first reflective film from an outside.

17 Claims, 12 Drawing Sheets

(51) Int. Cl.
*G01N 21/07* (2006.01)
*G01N 21/03* (2006.01)
*G01N 21/69* (2006.01)

(52) U.S. Cl.
CPC .. *B01L2300/0864* (2013.01); *B01L 2300/0893* (2013.01); *B01L 2300/168* (2013.01); *B01L 2400/0415* (2013.01); *G01N 2021/0346* (2013.01); *G01N 2201/0446* (2013.01); *G01N 2201/0612* (2013.01)

(56) References Cited

U.S. PATENT DOCUMENTS

| | | | |
|---|---|---|---|
| 2009/0251695 A1* | 10/2009 | Moriya | G01N 15/0211 356/336 |
| 2010/0006774 A1 | 1/2010 | Ohtsuka et al. | |
| 2010/0256004 A1 | 10/2010 | Tashiro et al. | |
| 2011/0189723 A1 | 8/2011 | Yamamura et al. | |
| 2011/0210094 A1* | 9/2011 | Gray | G02B 6/122 216/12 |
| 2012/0088249 A1 | 4/2012 | Jovanovich et al. | |

FOREIGN PATENT DOCUMENTS

| | | |
|---|---|---|
| JP | 2003-344286 A | 12/2003 |
| JP | 2006-322819 A | 11/2006 |
| WO | 2010/027003 A1 | 3/2010 |

OTHER PUBLICATIONS

Exteneded European Search Report dated Oct. 14, 2015 issued in European Patent Application No. 13859389.2.

* cited by examiner

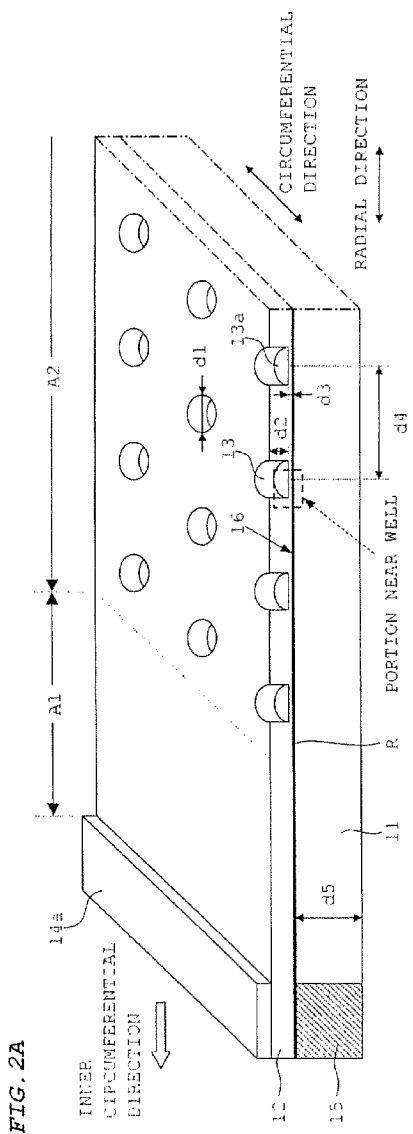
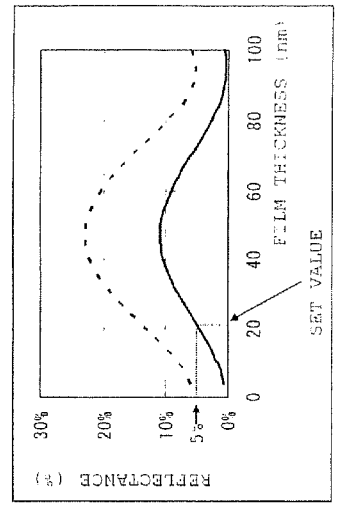
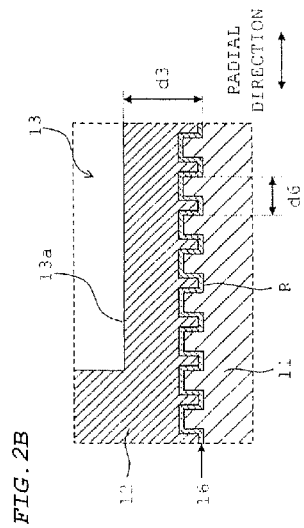
FIG. 2A
FIG. 2C
FIG. 2B

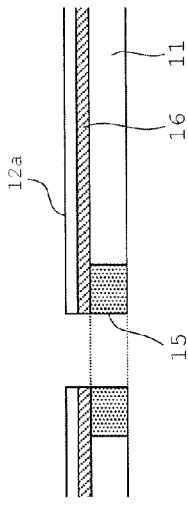
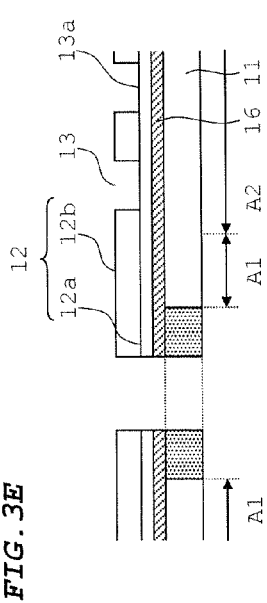
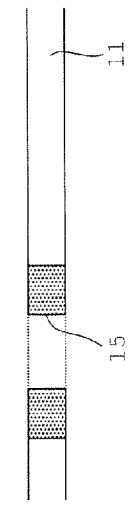
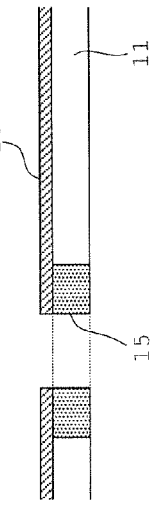
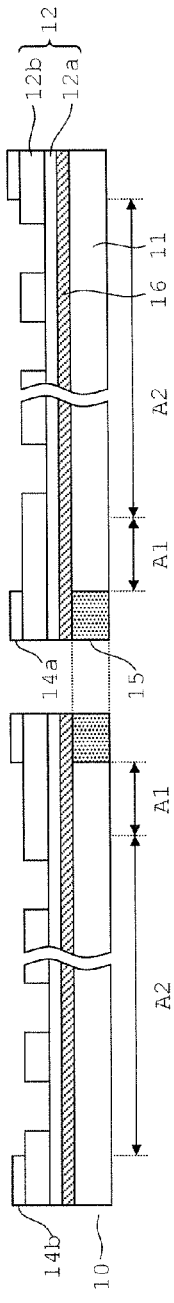
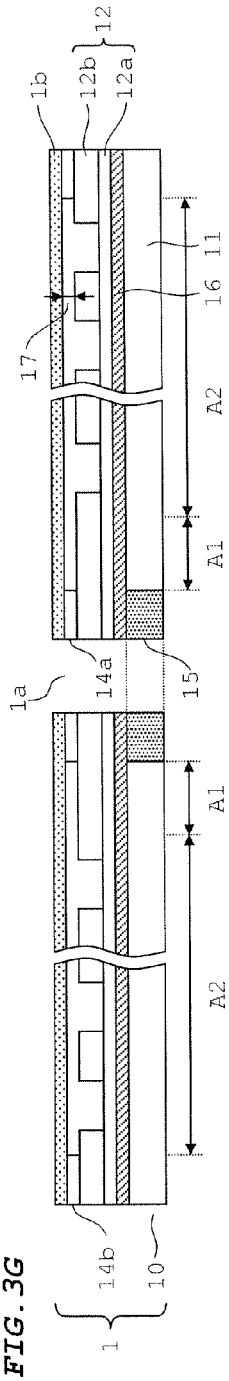
FIG. 3A
FIG. 3B
FIG. 3C
FIG. 3D
FIG. 3E
FIG. 3F
FIG. 3G

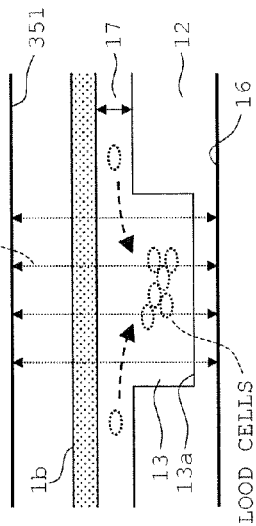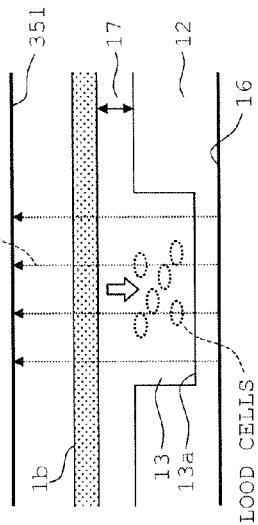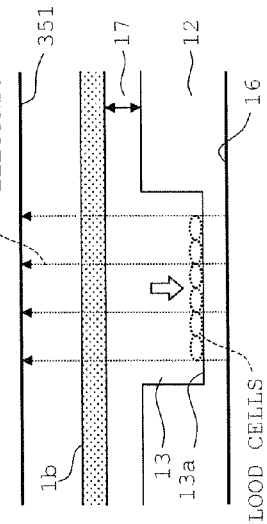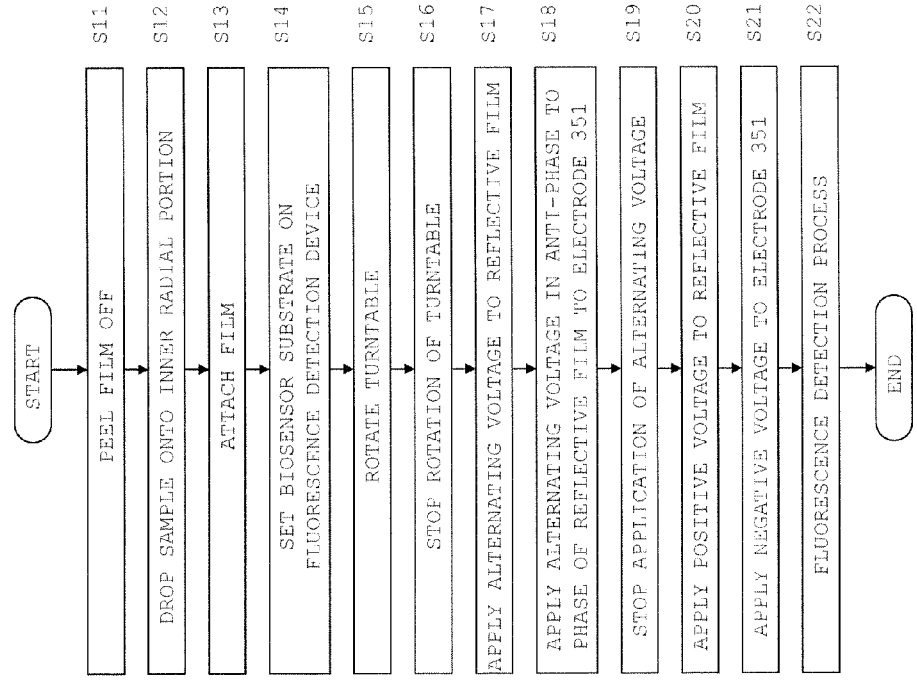

SAMPLE-HOLDING CARRIER AND FLUORESCENCE DETECTION DEVICE USING SAME

CROSS REFERENCE TO RELATED APPLICATION

This application is a continuation of International Application No. PCT/JP2013/006387 filed on Oct. 29, 2013, entitled "SAMPLE HOLDING CARRIER AND FLUORESCENCE DETECTION DEVICE USING SAME", which claims priority under 35 U.S.C. Section 119 of Japanese Patent Application No. 2012-263601 filed on Nov. 30, 2012, entitled "SAMPLE HOLDING CARRIER AND FLUORESCENCE DETECTION DEVICE USING SAME". The disclosure of the above application is incorporated herein by reference.

BACKGROUND OF THE INVENTION

1. Field of the Invention

The present invention relates to a sample holding carrier that holds a sample prepared by applying fluorescence labeling to a test sample such as a cell and a fluorescence detection device using the same.

2. Disclosure of Related Art

It is important specifically in the medical field such as a clinical site to detect a cell infected with pathogenic bacteria and a cell in a predetermined form from a large number of cells. As a method for quickly, easily, and highly accurately detecting such a cell, a method below is introduced, for example. In this method, a plurality of micro chambers (wells) is formed on a microarray chip, and fluorescently-labeled cells are filled in the wells. The wells are then observed through a fluorescence microscope while being irradiated with laser light, and a certain cell emitting fluorescence is detected.

Moreover, such a configuration is known in which a series of wells filled with cells is scanned with laser light to detect fluorescence emitted from the cells. In this configuration, a series of wells is formed in the circumferential direction of a disk, and a series of information pits is formed in tracks on a layer isolated on the light incident side from a layer on which the wells are formed as the information pits are arranged along the arrangement of the wells. Positional information (address information) is held on the information pit.

In this configuration, in an optical system that detects fluorescence, a light source for irradiating the wells with excitation light and a light source for irradiating the information pits with laser light are separately prepared, and light emitted from the light sources are converged through a shared objective lens. The objective lens is controlled in such a manner that the laser light for information pits is focused on the information pits and caused to follow a series of information pit strings (a track). Thus, the excitation light is focused on cells filled in the wells, and a series of the wells is in turn scanned with the laser light. Moreover, the optical system includes a photodetector that detects fluorescence emitted from cells and a photodetector that receives laser light modulated by the information pits. A signal for controlling the objective lens and a signal for reproducing information held on the information pit are generated from the output from the photodetector that receives the laser light.

When fluorescence is emitted from cells by irradiating the cells with the excitation light, this fluorescence is detected by the fluorescence detection photodetector. Moreover, the position of a well accommodating a cell that emits fluorescence is identified from positional information acquired from the information pit when fluorescence is detected. As described above, the presence or absence of a detection target cell and the position of a well accommodating the cell are automatically detected from a large number of cells accommodated in a series of the wells arranged on the disk without observation through a fluorescence microscope.

In the configuration like the latter in which wells are scanned with laser light to detect fluorescence emitted from cells, when observation target cells are laid on each other in a well, it is difficult to efficiently irradiate individual cells with excitation light. In this case, it is likely that fluorescence emitted from cells in the well is not enabled to be highly accurately detected.

SUMMARY OF THE INVENTION

A first aspect of the present invention relates to a sample-holding carrier. The sample-holding carrier according to the aspect includes: a substrate to which irradiation light is entered from an under face; a first reflective film disposed on a top face side of the substrate and having electrical conductivity; a sample accommodating portion disposed on a top face side of the first reflective film and having a bottom portion; and a first current carrying part configured to apply a voltage to the first reflective film from an outside.

A second aspect according to the present invention relates to a fluorescence detection device that irradiates a sample-holding carrier holding a sample applied with fluorescence labeling with irradiation light and detects fluorescence emitted from the sample by irradiating the sample-holding carrier with the irradiation light. Here, the sample-holding carrier includes: a substrate to which irradiation light is entered from an under face; a first reflective film disposed on a top face side of the substrate and having electrical conductivity; a sample accommodating portion disposed on a top face side of the first reflective film and having a bottom portion; and a first current carrying part configured to apply a voltage to the first reflective film from an outside. The fluorescence detection device according to the aspect includes: a light source configured to emit the irradiation light; an objective lens configured to converge the irradiation light on the sample-holding carrier; a photodetector configured to receive the irradiation light reflected by the first reflective film; a fluorescence detector configured to receive fluorescence emitted from the sample by irradiating the sample-holding carrier with the irradiation light; and a voltage applying unit configured to apply a voltage to the first reflective film through the first current carrying part.

BRIEF DESCRIPTION OF THE DRAWINGS

These and other objects, and novel features of the present invention will be more apparent from the description of an embodiment shown below with reference to the accompanying drawings below.

FIGS. 2A to 2C are a cross sectional view of a part of the biosensor substrate according to the first embodiment, an enlarged diagram of a portion near a well, and the simulation result of the reflectance of a reflection plane, respectively.

FIGS. 3A to 3G are diagrams of a fabrication method for the biosensor substrate according to the first embodiment.

FIGS. 8A to 8D are a flowchart of the procedures in performing a fluorescence detection process of the fluorescence detection device according to the first embodiment and diagrams of the state of red blood cells.

FIGS. 10A to 10H are diagrams of a fabrication method for a biosensor substrate according to a third embodiment.

Figures 1A, 1B:
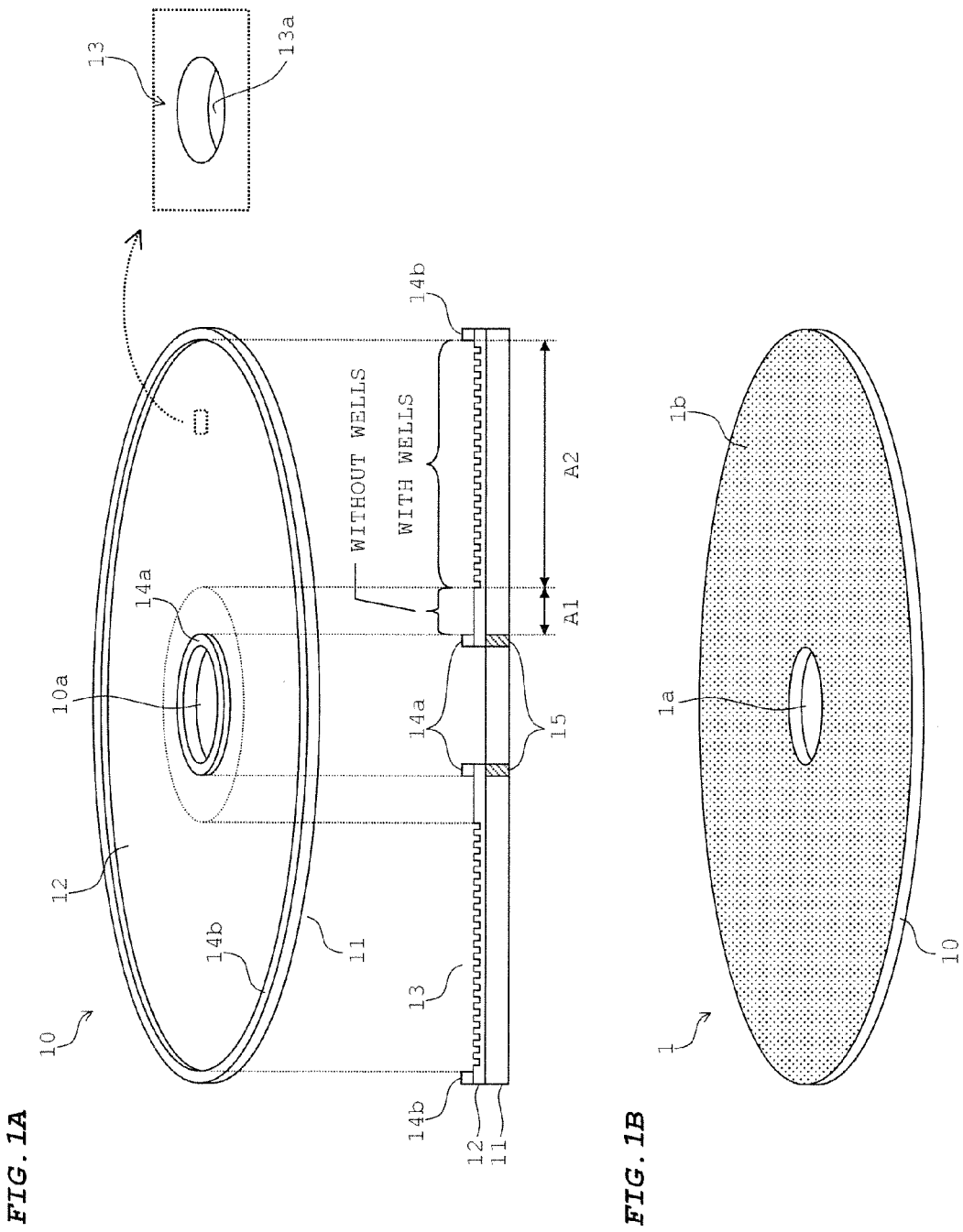
FIGS. 1A and 1B are schematic diagrams of the configurations of an accommodating body and a biosensor substrate according to a first embodiment, respectively.

However, the drawings are merely intended for description and are not intended to limit the scope of the invention.

DESCRIPTION OF PREFERRED EMBODIMENTS

A biosensor substrate and a fluorescence detection device according to embodiments are used for detecting red blood cells infected with malaria parasites. In the following, the embodiments of the present invention will be described with reference to the drawings.

In the embodiments described below, a biosensor substrate 1 corresponds to "a sample-holding carrier" according to the present invention. A film 1b corresponds to "a cover part" according to the present invention. A base substrate 11 corresponds to "a substrate" according to the present invention. A well 13 corresponds to "a sample accommodating portion" according to the present invention. A bottom face portion 13a corresponds to "a bottom portion" according to the present invention. A conductive ring 15 corresponds to "a first current carrying part" according to the present invention. Reflective films 16 and 25 correspond to "first reflective films" according to the present invention. A reflective film 23 corresponds to "a second reflective film" according to the present invention. A conductive ring 21 corresponds to "a second current carrying part" according to the present invention. An electrical conducting part 26 corresponds to "a first current carrying part" according to the present invention. A semiconductor laser 101 corresponds to "a light source" according to the present invention. A controller 205, a voltage supply circuit 206, a turntable 320, electrodes 321a, 321b, 322a, 322b, 331a, and 332a, a clamper 330, electrical conducting parts 341, 343, and 371, and support parts 342 and 372 correspond to "a voltage applying unit" according to the present invention. The correspondences between the present invention and the embodiment are only examples, and will not limit the present invention to the embodiment.

<First Embodiment>

FIG. 1A is a schematic diagram of the configuration of an accommodating body 10.

As illustrated in a perspective view on the upper side in FIG. 1A, the accommodating body 10 has a disk shape similarly to an optical disk (such as a CD and a DVD), and a circular hole 10a is formed in the center. As illustrated in the perspective view on the upper side and a cross sectional view on the lower side in FIG. 1A, the accommodating body 10 includes a base substrate 11, a well layer 12, shelf portions 14a and 14b, and a conductive ring 15. The conductive ring 15 in an annular shape is disposed on the hole on the inner radial portion of the base substrate 11. The well layer 12 is disposed on the top face side of the base substrate 11 and the conductive ring 15, and the inner radius side and the outer radius side of the well layer 12 are sectioned into regions A1 and A2, respectively.

As illustrated in an enlarged diagram on the right end in FIG. 1A, a plurality of micro wells 13 in a cylindrical hollow is formed on the region A2. The wells 13 are arranged nearly concentrically from the inner radius to the outer radius on the region A2 of the well layer 12. The well 13 has a bottom face portion 13a one step lower than the top face of the well layer 12, and the diameter and the height are set in such a manner that a sample can be accommodated. It is noted that the wells 13 are not formed on the region A1. Moreover, the shelf portions 14a and 14b in an annular shape are disposed on the innermost radial portion and the outermost radial portion of the well layer 12, respectively.

FIG. 1B is a schematic diagram of the configuration of a biosensor substrate 1.

The biosensor substrate 1 has a structure in which a film 1b in a thin film shape is disposed on the top face of the accommodating body 10 illustrated in FIG. 1A. A removable and reattachable adhesive is applied in advance on the innermost radial portion and the outermost radial portion on the under face of the film 1b (the regions facing the shelf portions 14a and 14b). Thus, a user can easily remove the film 1b from the accommodating body 10, and can again dispose the film 1b, which is removed from the accommodating body 10, on the accommodating body 10.

In using the biosensor substrate 1, the user first peels the film 1b off from the accommodating body 10, and then accommodates a sample prepared by applying fluorescence labeling to a test sample (red blood cells) in advance in the well 13. The user then again attaches the removed film 1b to the accommodating body 10, and sets the biosensor substrate 1 on a fluorescence detection device 100, described later. The set biosensor substrate 1 is irradiated with laser light emitted from the semiconductor laser 101, described later, (in the following, referred to as "excitation light") from the under face side. Thus, when the red blood cells to which fluorescence labeling is applied are infected with malaria parasites, fluorescence is emitted from malaria parasites. The procedures of accommodating a sample in the well 13 will be described later with reference to FIGS. 4A to 4C. The fluorescence detection device 100 will be described later with reference to FIG. 5.

FIG. 2A is a cross sectional view of a part of the biosensor substrate 1, and FIG. 2B is an enlarged diagram of a portion near the well (a portion shown in a broken line frame) in FIG. 2A.

A spiral track similar to an optical disk is formed on the top face of the base substrate 11 (the face on the well layer 12 side). The track is formed of a groove that is a meandering groove. The groove holds address information that identifies the position on the surface of the biosensor substrate 1 in the meandering shape of the groove (wobble). Moreover, information unique to the biosensor substrate 1, as well as the address information, is held on the track portion corresponding to the region A1 in the meandering shape of the groove.

An electrically conductive reflective film 16 is disposed between the well layer 12 and each of the base substrate 11 and the conductive ring 15. The reflective film 16 is formed on the track on the top face of the base substrate 11, and a reflection plane R that is the interface between the reflective film 16 and the base substrate 11 is formed on the top face of the base substrate 11. The material and film thickness of the reflective film 16 are set in such a manner that the reflectance of the reflection plane R becomes higher with respect to the wavelength of the excitation light and the reflectance of the reflection plane R becomes lower with respect to the wavelength of fluorescence. The well 13 is formed on the top face side of the well layer 12 as a predetermined spacing is provided. The bottom face portion 13a of the well 13 is positioned slightly on the upper side of the reflective film 16, and spaced from the top face of the reflective film 16.

Here, suppose that the diameter and height of the well 13 are defined as d1 and d2, respectively, the spacing between the bottom face portion 13a and the reflection plane R is defined as d3, the spacing between the wells 13 is defined as d4, the thickness of the base substrate 11 is defined as d5, and the track pitch on the reflection plane R is defined as d6. In the embodiment, d1 to d6 are set to 100 μm, 50 μm, 2 μm, 300 μm, 0.6 mm, and 1 μm, respectively. It is noted that the diameter and thickness of a red blood cell, which is a test sample in the embodiment are about 10 μm and about 2 μm, respectively. Therefore, a plurality of red blood cells can be disposed on the bottom face portion 13a of the well 13.

Moreover, the base substrate 11 is formed of polycarbonate, the well layer 12 is formed of polydimethylsiloxane (PDMS), and the reflective film 16 is formed of ZnO. ZnO is suited to the material of the reflective film 16 because fluorescence is not easily emitted from ZnO with excitation light and noise light caused in the detection of fluorescence from a sample is small. The film thickness of the reflective film 16 is preferably in a range of 5 to 100 nm from the viewpoint of manufacture.

FIG. 2C is simulation results of the reflectance of the reflection plane R with respect to the wavelength of the excitation light when the film thickness of the reflective film 16 is changed. A broken line expresses the case where the well layer 12 is not formed on the upper part of the reflective film 16, and a solid line expresses the case where the well layer 12 is formed on the upper part of the reflective film 16 similarly to the embodiment.

In the fluorescence detection device 100 described later, in order to enable stable acquisition of address information and the like based on the reflected light of the excitation light caused by the reflective film 16, the reflectance is desirably equal to or greater than the reflectance on the surface of the base substrate 11. More specifically, the reflectance on the reflective film 16 is desirably 5% or more. Therefore, based on FIG. 2C, in the case where the well layer 12 is formed on the upper part of the reflective film 16, the film thickness of the reflective film 16 is desirably in the range from 20 to 70 nm. Moreover, when the film thickness of the reflective film 16 is 40 nm or greater, an increase in the reflectance is slowed as illustrated in FIG. 2C and the film thickness is increased due to the increased thickness. On this account, the film thickness of the reflective film 16 is more desirably in the range from 20 to 40 nm, and in the embodiment, the film thickness is set to 20 nm. In this case, the resistance value of the reflective film 16 is $2\times10^{-4}$ Ω cm. Furthermore, when the film thickness is set in a range of 20 to 40 nm, the reflective film 16 can be formed along the groove formed on the top face of the base substrate 11.

Here, in the case where a metal material such as Al is used for the material of the reflective film 16, the reflectance is higher than the reflectance of ZnO. Thus, it is necessary to form a very thin film having a film thickness of less than 5 nm in order to sufficiently irradiate a sample with excitation light after transmitting the excitation light through the reflective film 16, and it is difficult to stably form the film. On the other hand, in the case where a material having a reflectance lower than the reflectance of ZnO, it is necessary to increase the film thickness in order to obtain a sufficient reflectance, and manufacturing costs are increased. Therefore, in order to suppress manufacturing costs and to obtain an appropriate reflectance, ZnO is suited to the material of the reflective film 16.

FIGS. 3A to 3G are diagrams of a fabrication method for the biosensor substrate 1.

First, as illustrated in FIG. 3A, the base substrate 11 is formed by injection molding. A series of the tracks is formed on the top face of the base substrate 11 by this injection molding. Subsequently, as illustrated in FIG. 3B, the conductive ring 15 in an annular shape is attached to the hole formed in the center of the base substrate 11. Subsequently, as illustrated in FIG. 3C, the reflective film 16 is formed on the top faces of the base substrate 11 and the conductive ring 15. Thus, the reflective film 16 and the conductive ring 15 are in an electrically connected state.

Subsequently, as illustrated in FIG. 3D, a bottom face layer 12a having a thickness d3 and formed of PDMS is disposed on the top face of the reflective film 16. Subsequently, as illustrated in FIG. 3E, a top face layer 12b having a thickness d2 and formed of PDMS is disposed on the top face of the bottom face layer 12a. A hole corresponding to the well 13 is formed in advance on the top face layer 12b. In this manner, a plurality of the wells 13 is formed, and the well layer 12 is formed in the combination of the bottom face layer 12a and the top face layer 12b. Subsequently, as illustrated in FIG. 3F, the shelf portions 14a and 14b are disposed on the top faces of the innermost radial portion and the outermost radial portion of the well layer 12, respectively. In this manner, the accommodating body 10 is completed.

Subsequently, a removable and reattachable adhesive is applied to the innermost radial portion and the outermost radial portion of the under face of the film 1b, and the film 1b is attached to the accommodating body 10 in such a manner that the under face of the film 1b is supported only by the shelf portions 14a and 14b with respect to the accommodating body 10 as illustrated in FIG. 3G. Thus, a gap 17 is provided between the top face layer 12b of the well layer 12 and the film 1b. In this manner, the biosensor substrate 1 is completed.

Figure 4A:
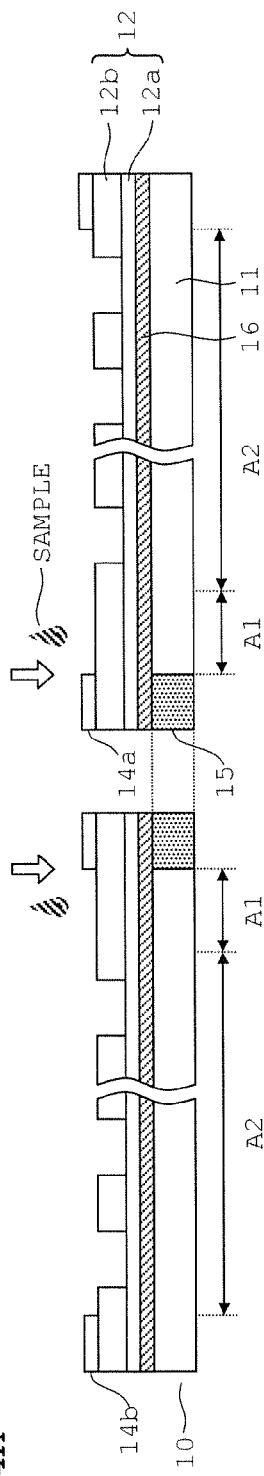
FIGS. 4A to 4C are diagrams of the procedures of accommodating a sample in the biosensor substrate according to the first embodiment.
Figure 4B:
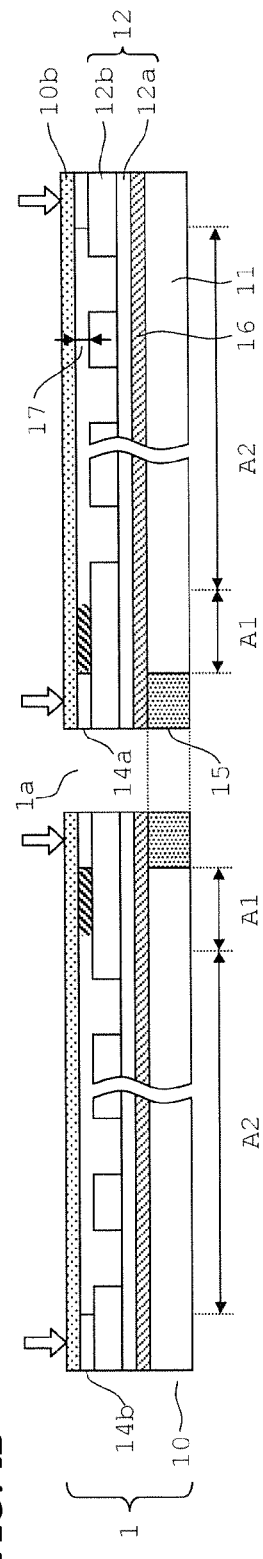
Figure 4C:
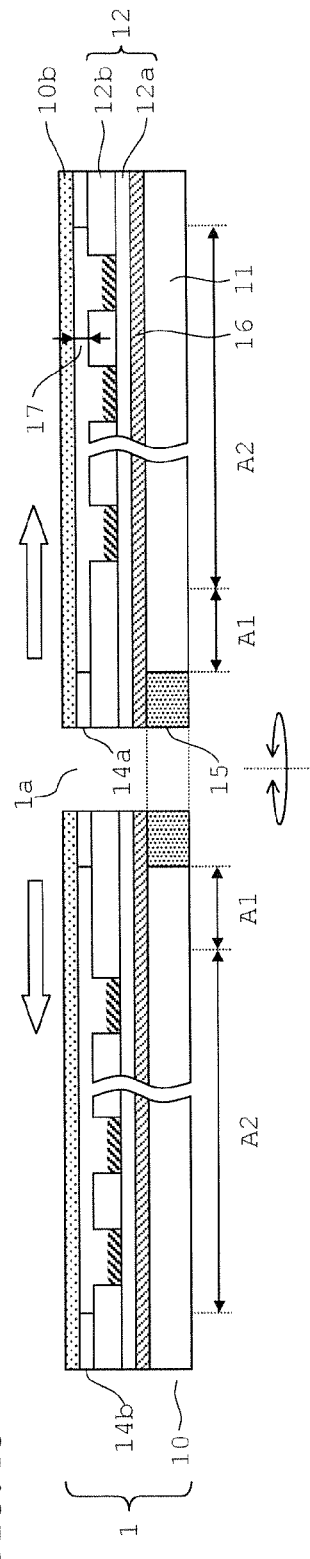

FIGS. 4A to 4C are diagrams of the procedures of accommodating a sample in the biosensor substrate 1.

As illustrated in FIG. 4A, the user first peels the film 1b off from the accommodating body 10, and drops a sample onto the region A1 of the well layer 12. Subsequently, as illustrated in FIG. 4B, the user again attaches the removed film 1b to the accommodating body 10. Subsequently, when this biosensor substrate 1 is set on the fluorescence detection device 100 (see FIG. 5) and the biosensor substrate 1 is rotated by the fluorescence detection device 100, the sample on the region A1 of the well layer 12 is moved in the outer circumferential direction by centrifugal force. At this time, since the upper part of the accommodating body 10 is sealed by the film 1b, the sample is not scattered to the outside. Moreover, when centrifugal force is applied, the sample is dispersed and moved in the outer circumferential direction through the gap 17, and entered to a plurality of the wells 13 on the region A2 of the well layer 12. In this manner, as illustrated in FIG. 4C, the sample is accommodated in the wells 13.

Figure 5:
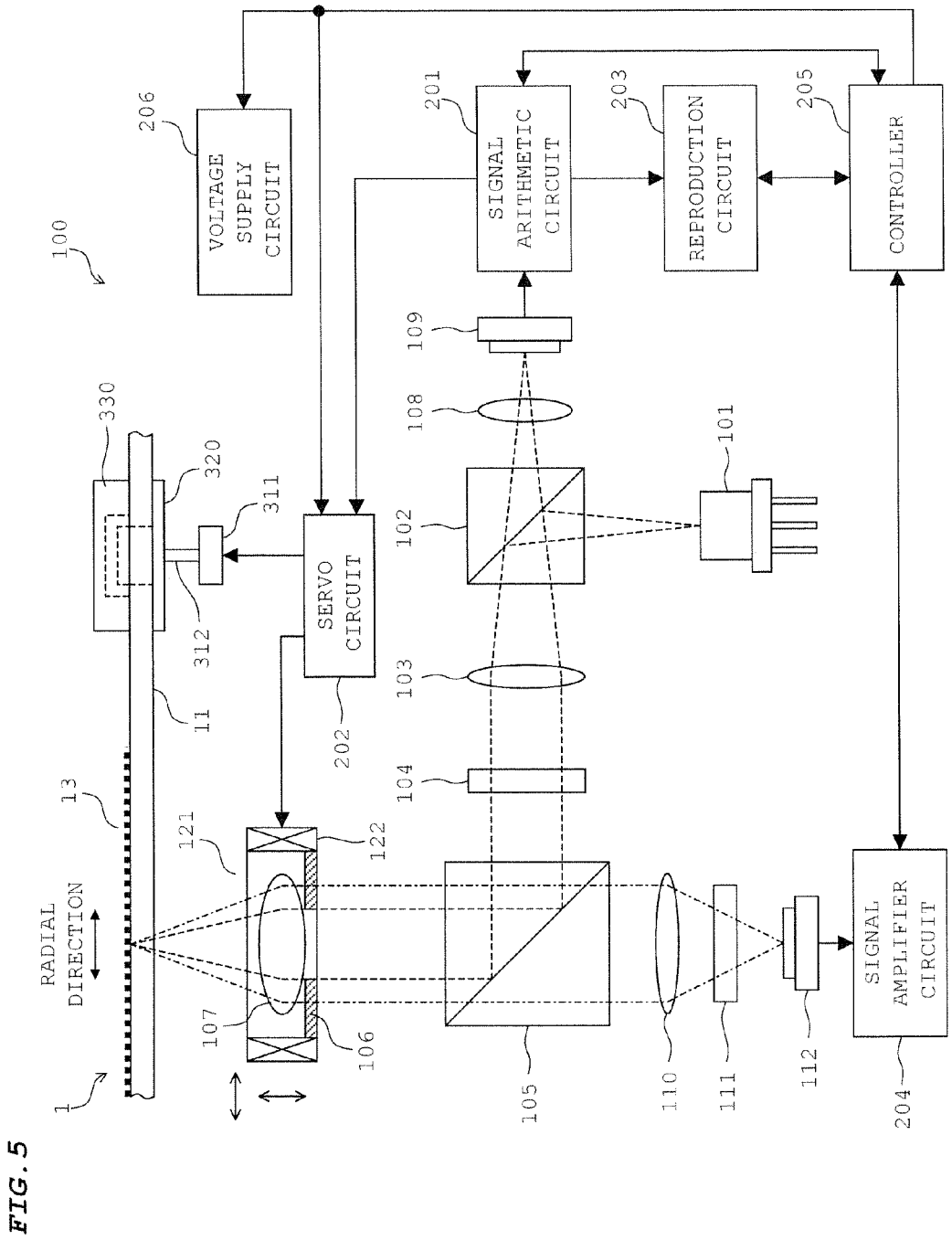
FIG. 5 is a diagram of the configuration of a fluorescence detection device according to the first embodiment.

FIG. 5 is a diagram of the configuration of the fluorescence detection device 100 according to the embodiment.

The optical system of the fluorescence detection device 100 includes a semiconductor laser 101, a polarized beam splitter (PBS) 102, a collimator lens 103, a quarter-wave plate 104, a dichroic prism 105, an aperture 106, an objective lens 107, an anamorphic lens 108, a photodetector 109, a condenser lens 110, a filter 111, and a fluorescence detector 112. Moreover, in addition to the optical system, the fluorescence detection device 100 includes a holder 121, an objective lens actuator 122, a signal arithmetic circuit 201, a servo circuit 202, a reproduction circuit 203, a signal amplifier circuit 204, a controller 205, a voltage supply circuit 206, a motor 311, a spindle 312, a turntable 320, and a clamper 330. Furthermore, as illustrated in FIG. 7C, the fluorescence detection device 100 includes an upper casing 350, a lower casing 360, an electrical conducting part 341, and a support part 342.

It is noted that the optical system, the holder 121, and the objective lens actuator 122 of the fluorescence detection device 100 are disposed in a housing similarly to existing optical pickup devices for use in the recording/reproduction of a CD and a DVD. Moreover, this housing is movable in the radial direct ion of the biosensor substrate 1 by a predetermined guide mechanism.

The semiconductor laser 101 emits laser light (excitation light) at a wavelength of about 405 nm. It is noted that excitation light in the embodiment is an example of irradiation light recited in claims. In FIG. 5, excitation light guided to the biosensor substrate 1 is depicted by broken lines in excitation light emitted from the semiconductor laser 101. The position of the semiconductor laser 101 is adjusted in such a manner that the excitation light emitted from the semiconductor laser 101 is an S-polarized light with respect to the PBS 102. Thus, the excitation light emitted from the semiconductor laser 101 is reflected by the PBS 102, and entered to the collimator lens 103.

The collimator lens 103 converts the excitation light entered from the PBS 102 side into collimated light. Thus, the excitation light passed through the collimator lens 103 is collimated light in a predetermined diameter. The quarter-wave plate 104 converts the excitation light entered from the collimator lens 103 side into circular polarized light, and converts the excitation light entered from the dichroic prism 105 side into linear polarized light orthogonal to the polarization direction when entered from the collimator lens 103 side. Thus, the excitation light entered from the collimator lens 103 side to the PBS 102 is transmitted through the PBS 102.

The dichroic prism 105 is configured to reflect light at a wavelength of about 405 nm and to transmit light in a range of wavelengths from about 450 to 540 nm. Thus, the excitation light entered from the quarter-wave plate 104 side is reflected by the dichroic prism 105, and entered to the aperture 106. The aperture 106 has wavelength selectivity, and the aperture 106 is formed with an opening in a circular shape having a predetermined diameter. Thus, a predetermined peripheral portion of the excitation light entered to the aperture 106 is shielded, and fluorescence entered to the aperture 106 is all transmitted.

The objective lens 107 is configured to accurately converge the excitation light on the biosensor substrate 1. More specifically, the objective lens 107 is configured in which the excitation light entered from the aperture 106 side is converged at a predetermined NA (numerical aperture, 0.34, here). The incident diameter of the excitation light with respect to the objective lens 107 is determined by the diameter of the aperture 106. The focal depth of the excitation light converged through the objective lens 107 is determined by the NA of the excitation light. The focal depth of the excitation light will be described later with reference to FIGS. 6A and 6B.

The objective lens 107 is driven by the objective lens actuator 122 in the focus direction (the direction perpendicular to the biosensor substrate 1) and the tracking direction (the radial direction of the biosensor substrate 1) in the state in which the objective lens 107 is held on the holder 121. In other words, the objective lens 107 is driven to follow the track formed of a groove in the state in which the excitation light is focused on the reflection plane R of the biosensor substrate 1. A part of the excitation light focused on the reflection plane R is reflected by the reflection plane R, and most of the excitation light is transmitted through the reflection plane R.

In the irradiation light applied to the biosensor substrate 1, the excitation light reflected by the reflection plane R (in the following, referred to as "the reflected excitation light") is reflected by the dichroic prism 105, converted into linear polarized light through the quarter-wave plate 104, and formed in converged light at the collimator lens 103. The reflected excitation light entered from the collimator lens 103 side to the PBS 102 is then transmitted through the PBS 102 as described above.

The anamorphic lens 108 introduces astigmatism to the reflected excitation light entered from the PBS 102 side. The reflected excitation light transmitted through the anamorphic lens 108 is entered to the photodetector 109. The photodetector 109 includes a quadrant sensor that receives the reflected excitation light on a light receiving surface. The detection signal of the photodetector 109 is inputted to the signal arithmetic circuit 201.

When the excitation light converged through the objective lens 107 is scanned over the position corresponding to the well 13, the excitation light transmitted through the reflection plane R in the excitation light applied to the biosensor substrate 1 reaches the bottom face portion 13a of the well 13. When red blood cells, which are disposed on the bottom face portion 13a, applied with fluorescence labeling, and infected with malaria parasites, are irradiated with the excitation light, fluorescence is emitted from malaria parasites. As depicted by an alternate long and short dash line in FIG. 5, the NA (numerical aperture) of this fluorescence is greater than the NA of the excitation light. On this account, the beam diameter of fluorescence is greater than the beam diameter of the excitation light between the objective lens 107 and the dichroic prism 105. The NA of fluorescence is 0.65, for example. Moreover, the wavelength of fluorescence is different from the wavelength of the excitation light, and is in the range of wavelengths from 450 to 540 nm in the embodiment.

Fluorescence transmitted through the aperture 106 and entered to the dichroic prism 105 is transmitted through the dichroic prism 105. The condenser lens 110 condenses fluorescence entered from the dichroic prism 105 side, and guides the fluorescence to the fluorescence detector 112. The filter 111 is a bandpass filter of a narrow band, and transmits only fluorescence emitted from red blood cells infected with malaria parasites. The fluorescence detector 112 includes a sensor that receives fluorescence transmitted through the filter 111. The detection signal of the fluorescence detector 112 is inputted to the signal amplifier circuit 204.

The signal arithmetic circuit 201 generates a focus error signal FE and a tracking error signal TE from the detection signal of the photodetector 109, and generates a wobble signal corresponding to the meandering shape of the track from the detection signal of the photodetector 109.

The servo circuit 202 controls the driving of the objective lens actuator 122 using the focus error signal FE and the tracking error signal TE outputted from the signal arithmetic circuit 201. Moreover, the servo circuit 202 controls the movement of the housing in which the optical system of the fluorescence detection device 100, the holder 121, and the objective lens actuator 122 are disposed. Furthermore, the servo circuit 202 controls the motor 311 using the wobble signal outputted from the signal arithmetic circuit 201 in such a manner that the biosensor substrate 1 is rotated at a constant linear velocity. The reproduction circuit 203 demodulates the wobble signal outputted from the signal arithmetic circuit 201, and generates reproduction data. The signal amplifier circuit 204 amplifies the detection signal of the fluorescence detector 112.

The controller 205 controls the signal arithmetic circuit 201, the servo circuit 202, and the reproduction circuit 203 as well as the units of the fluorescence detection device 100. The controller 205 detects fluorescence emitted from the region A2 based on the output signal of the signal amplifier circuit 204, and determines the position at which fluorescence is emitted based on the detected fluorescence and the reproduction data (the address information) of the track outputted from the reproduction circuit 203. Moreover, the controller 205 stores address information corresponding to the position at which fluorescence is emitted from the region A2 on an internal memory. Furthermore, the controller 205 acquires reproduction data (system information) outputted from the reproduction circuit 203, and stores the data on the internal memory. Here, the system information includes information about the wavelength and use power of the excitation light corresponding to the biosensor substrate 1, the arrangement of the wells, the number of revolutions of the substrate, the version of the specification, and the like.

The voltage supply circuit 206 supplies a voltage to the turntable 320 and the upper casing 350. The supply of the voltage by the voltage supply circuit 206 will be described later with reference to FIGS. 7A to 7D. The motor 311 rotates the spindle 312 according to the control of the servo circuit 202. The turntable 320 is pivotally supported on the spindle 312, and the turntable 320 supports the under face (the under face of the base substrate 11) of the biosensor substrate 1 from the lower side, and supports the hole 1a of the biosensor substrate 1. The clamper 330 fixes the biosensor substrate 1 placed on the turntable 320 from the upper side. The turntable 320 and the clamper 330 are rotated integrally with the biosensor substrate 1.

In the case where the fluorescence detection device 100 thus configured is used to detect fluorescence, the user sets the biosensor substrate 1 on which the sample is accommodated in the turntable 320. The turntable 320 is then rotated, and the sample accommodated in the region A1 of the well layer 12 as illustrated in FIG. 43 is moved to the wells 13 as illustrated in FIG. 4C. After that, the biosensor substrate 1 is irradiated with the excitation light.

Figure 6A:
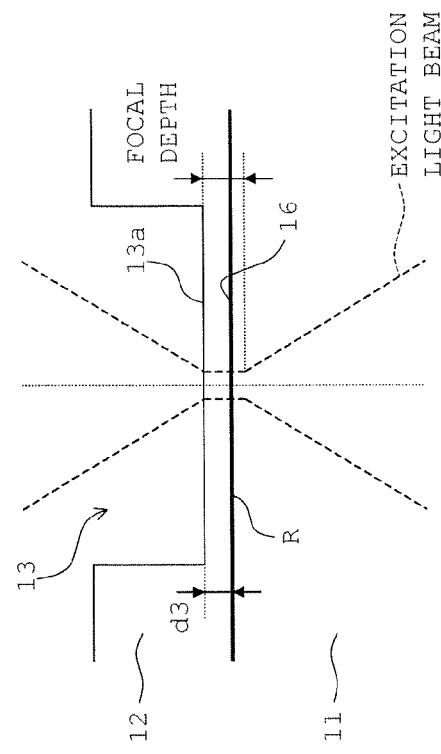
FIGS. 6A and 6B are diagrams illustrative of the focal depth of excitation light according to the first embodiment.
Figure 6B:
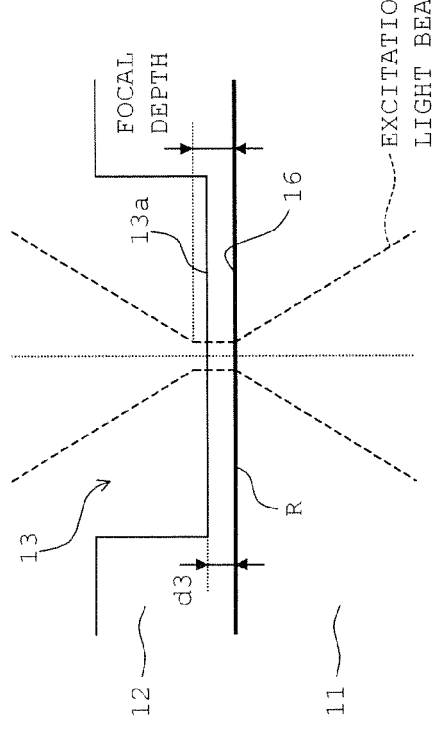

FIGS. 6A and 6B are diagrams illustrative of the focal depth of the excitation light. FIG. 6A shows the state in which the lowest point in the range of the focal depth of the excitation light is matched with the reflective film 16, and FIG. 6B shows the state in which the highest point in the range of the focal depth of the excitation light is matched with the bottom face portion 13a.

As described above, the wavelength of the excitation light is 405 nm, and the NA of the excitation light (numerical aperture) is 0.34. Generally, the focal depth can be calculated by an expression, wavelength/(NA×NA). Thus, the focal depth of the excitation light in the embodiment is about 3.5 μm. The spacing d3 between the bottom face portion 13a and the reflection plane R illustrated in FIGS. 2A and 2B is set smaller than the focal depth of the excitation light, and is set 2.0 μm here. When the NA of the excitation light is set as described above, the spot diameter at the focal position is about 1 μm. The spacing d6 of the track pitch illustrated in FIG. 2B is set to 1 μm as the spacing d6 is almost the same as this spot diameter.

Since the spacing d3 between the bottom face portion 13a of the well 13 and the reflection plane R is 2 μm and the focal depth of the excitation light is 3.5 μm in the states in FIGS. 6A and 6B, both of the bottom face portion 13a and the reflection plane R are included in the range corresponding to the focal depth of the excitation light. Therefore, when the focal position of the excitation light is positioned at the reflection plane R using the focus servo, the light is also focused on the sample disposed on the bottom face portion 13a.

Here, as illustrated in FIG. 4B, when the sample (red blood cells to which fluorescence labeling is applied) dropped on the region A1 of the well layer 12 is moved to the wells 13 as illustrated in FIG. 4C, the red blood cells are likely to be laid on one another in the wells 13. When red blood cells are laid on one another in the wells 13, it is difficult to efficiently irradiate the individual cells with the excitation light, and it is likely that fluorescence emitted from the red blood cells in the wells 13 is not enabled to be highly accurately detected.

Therefore, in the embodiment, a positive voltage is applied to the reflective film 16 from the voltage supply circuit 206 based on the fact that red blood cells are generally negatively charged, and then the red blood cells are attracted to the bottom face portion 13a of the well 13. In other words, electric charges of a polarity opposite to the polarity of electric charges stored in red blood cells (cells) are applied to the reflective film 16, and the red blood cells are electrostatically captured on the bottom portion of the well 13. By this capture, the red blood cells are uniformly arranged on the bottom face portion 13a, and the individual red blood cells can be efficiently irradiated with the excitation light. In the following, the configuration and procedures of positioning red blood cells on the bottom face portion 13a will be described.

Figure 7B:
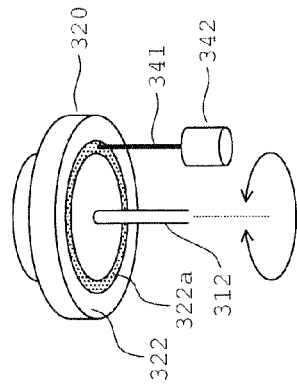
FIGS. 7A to 7D are schematic diagrams of the configuration of a turntable according to the first embodiment and schematic diagrams of the configuration of a cover.
Figure 7A:
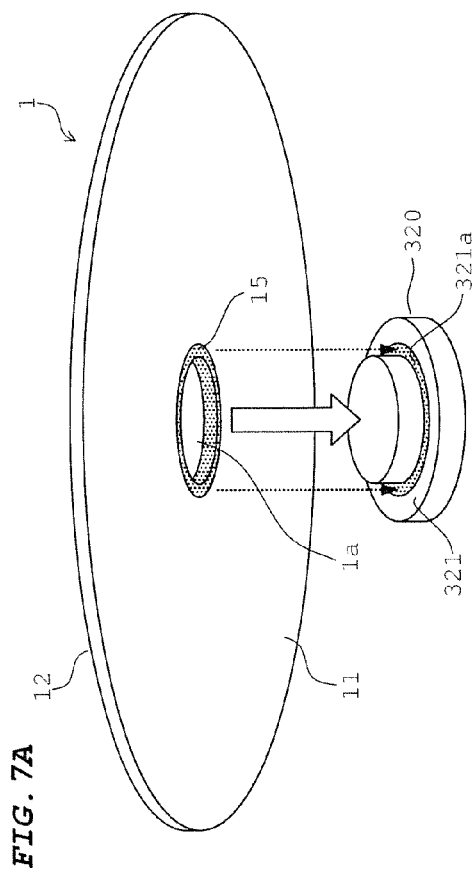

FIGS. 7A and 7B are schematic diagrams of the configuration of the turntable 320.

Referring to FIG. 7A, an electrode 321a in an annular shape is disposed on a top face 321 of the turntable 320 at a position opposite to the conductive ring 15 of the biosensor substrate 1. When the biosensor substrate 1 is set on the turntable 320, the conductive ring 15 of the biosensor substrate 1 is electrically connected to the electrode 321a.

Referring to FIG. 7B, an electrode 322a in an annular shape is disposed on an under face 322 of the turntable 320. The electrodes 321a and 322a are electrically connected to each other in the interior of the turntable 320. Moreover, in the fluorescence detection device 100, the electrical conducting part 341 and the support part 342 that supports the electrical conducting part 341 are disposed on the lower side of the under face 322. The electrical conducting part 341 is formed of an electrically conductive member having elasticity, and biased from the lower side by the support part 342 as the conducting part 341 is contacted with the electrode 322a. As illustrated in FIG. 7C, a voltage is applied to the electrical conducting part 341 from the voltage supply circuit 206 through the support part 342.

The turntable 320 is thus configured, and the voltage supplied to the electrical conducting part 341 is supplied to the conductive ring 15 through the electrodes 321a and 322a even in the case where the turntable 320 is rotated by the spindle 312. Thus, the voltage is supplied to the reflective film 16 electrically connected to the conductive ring 15.

Figure 7D:
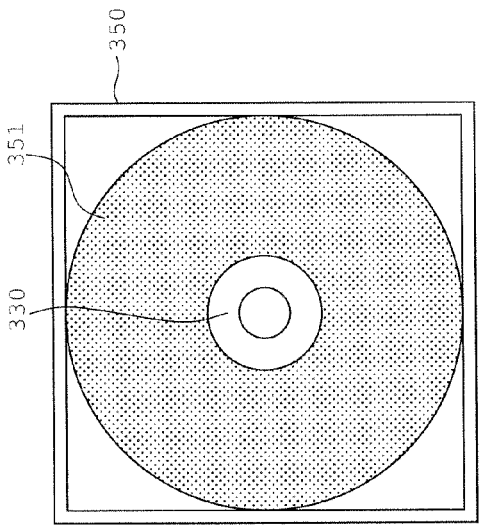
Figure 7C:
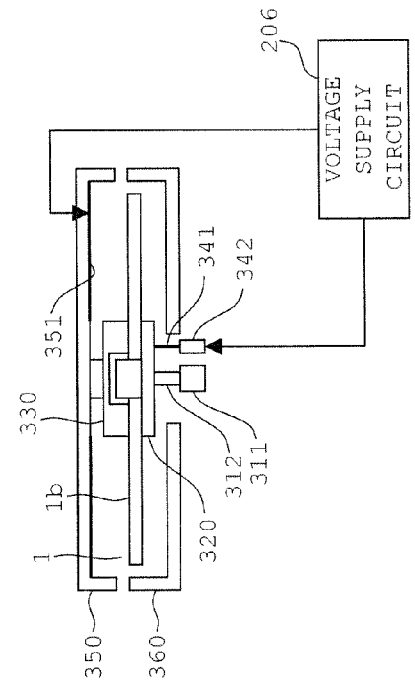

FIGS. 7C and 7D are schematic diagrams of the configuration of the upper casing 350. FIG. 7C is a perspective view of the fluorescence detection device 100 when viewed from the lateral direction, and FIG. 7D is a diagram of the upper casing 350 when viewed from the lower side.

Referring to FIG. 7C, the upper casing 350 and the lower casing 360 are disposed so as to cover the top face side and under face side of the biosensor substrate 1 set on the turntable 320, respectively. The upper casing 350 is openably and closably configured in which the user can attach and detach the biosensor substrate 1 to and from the turntable 320.

Referring to FIGS. 7C and 7D, the clamper 330 is disposed on the upper casing 350 in such a manner that when the biosensor substrate 1 is set and the upper casing 350 is closed, the clamper 330 fixes the biosensor substrate 1 from the upper side, and can be rotated with the rotation of the biosensor substrate 1. An electrode 351 in an annular shape is disposed on the under face of the upper casing 350 as the electrode 351 is opposite to the biosensor substrate 1. A voltage is applied to the electrode 351 from the voltage supply circuit 206.

FIG. 8A is a flowchart of the procedures in performing a fluorescence detection process.

As illustrated in FIG. 4A, first, the user peels the film 1b off from the biosensor substrate 1 (S11), and drops a sample onto the inner radial portion (the region A1 of the well layer 12) (S12). As illustrated in FIG. 4B, the user then again attaches the film 1b to the accommodating body 10 onto which the sample is dropped (S13). Subsequently, the user opens the upper casing 350 of the fluorescence detection device 100, sets the biosensor substrate 1 on the turntable 320, and closes the upper casing 350 (S14), and inputs an instruction to the fluorescence detection device 100 to start the operation. Thus, the controller 205 of the fluorescence detection device 100 reads information unique to the biosensor substrate 1 (system information) from the track portion corresponding to the region A1, and the operation of preparing fluorescence detection is started.

When the operation of preparing fluorescence detection is started, the controller 205 rotates the turntable 320 (S15) and moves the sample positioned at the inner radial portion in the outer circumferential direction by centrifugal force. Thus, as illustrated in FIG. 4C, the sample is moved in the wells 13. After a lapse of a predetermined time period, the controller 205 stops the rotation of the turntable 320 (S16)

Subsequently, the controller 205 applies an alternating voltage to the reflective film 16 (S17), and applies an alternating voltage in an anti-phase to the phase of the alternating voltage applied to the reflective film 16 to the electrode 351 (S18). Since the orientation of an electric field generated by the application is changed between upward and downward directions as matched with the cycle of the alternating voltage, polarizations are taken place in red blood cells, polarizations are attracted to each other, and the red blood cells are aggregated. At this time, as illustrated in FIG. 8B, red blood cells remaining in the gap 17 are gathered on the wells 13, and aggregated in the wells 13. After a lapse of a predetermined time period, the controller 205 stops the application of the alternating voltage to the reflective film 16 and the electrode 351 (S19).

Subsequently, the controller 205 applies a positive voltage to the reflective film 16 (S20), and applies a negative voltage opposite to the reflective film 16 to the electrode 351 (S21). Since the orientation of an electric field generated by the application is the upward direction, red blood cells generally negatively charged are attracted to the bottom face portion 13a as illustrated in FIG. 8C. In this manner, as illustrated in FIG. 8D, the red blood cells are uniformly arranged on the bottom face portion 13a. As described above, after the red blood cells are uniformly arranged on the bottom face portion 13a, the controller 205 rotates the turntable 320, irradiates the biosensor substrate 1 with excitation light, and starts the fluorescence detection process (S22).

<Effect of First Embodiment>

According to the embodiment, the following effect can be exerted.

When the sample (red blood cells to which fluorescence labeling is applied) dropped on the region A1 of the well layer 12 as illustrated in FIG. 4B is moved to the wells 13 as illustrated in FIG. 4C, the red blood cells are likely to be laid on one another in the wells 13. However, when a positive voltage is applied to the reflective film 16 based on the fact that red blood cells are generally negatively charged as illustrated in FIG. 8C, the red blood cells are attracted to the bottom face portion 13a, and uniformly arranged on the bottom face portion 13a as illustrated in FIG. 8D. Thus, the red blood cells in the wells 13 can be efficiently irradiated with the excitation light in the fluorescence detection process (S22 in FIG. 8A). Therefore, fluorescence emitted from red blood cells infected with malaria parasites can be highly accurately detected. Moreover, the red blood cells are uniformly arranged on the bottom face portion 13a, so that the number of red blood cells at positions irradiated with the excitation light can be made constant.

Furthermore, the electrode 351 is disposed on the under face of the upper casing 350 as the electrode 351 is opposite to the biosensor substrate 1, and a negative voltage is applied to the electrode 351 in the case where a positive voltage is applied to the reflective film 16. Thus, an electric field clearly directed to the upward direction is generated as illustrated in FIG. 8C as compared with the case where a voltage is applied only to the reflective film 16, so that red blood cells can be more surely attracted to the bottom face portion 13a.

In addition, after the sample is dropped onto the region A1 of the well layer 12, the film 1b is attached to the upper part of the accommodating body 10 as illustrated in FIG. 4B. Thus, even though the biosensor substrate 1 is rotated by the clamper 330 as illustrated in FIG. 4C, the sample can be prevented from being scattered to the outside. Moreover, it is possible to prevent undesirable discharge (unintended discharge) or evaporation of the sample from the well 13.

Furthermore, after the sample dropped onto the region A1 of the well layer 12 is accommodated in the wells 13 by centrifugal force as illustrated in FIG. 4C, an alternating voltage is applied to the reflective film 16, and an alternating voltage in an anti-phase to the phase of the alternating voltage applied to the reflective film 16 is applied to the electrode 351. Thus, as illustrated in FIG. 8B, red blood cells remaining in the gap 17 are gathered on the wells 13, and aggregated in the wells 13, so that most of the dropped sample can be efficiently accommodated in the wells 13.

It is noted that in the embodiment, the electrode 351 is disposed on the under face of the upper casing 350 as the electrode 351 is opposite to the reflective film 16. However, the electrode 351 maybe omitted, and S17 and S20 may be omitted from the procedures illustrated in FIG. 8A. Also in this case, it is possible that red blood cells are aggregated in the wells 13 using an alternating voltage applied to the reflective film 16 and the red blood cells are uniformly arranged on the bottom face portion 13a using a positive voltage applied to the reflective film 16. However, in this case, since the orientation of the electric field generated between the reflective film 16 and the electrode 351 is not so clear as compared with the embodiment, the electrode 351 is desirably disposed.

<Second Embodiment>

In the first embodiment described above, a voltage is applied to the sample from the upper side of the reflective film 16 from the electrode 351 disposed on the under face of the upper casing 350. In this embodiment, a film 1b is formed of a material having electrical conductivity, a voltage is applied to the film 1b, and thus a voltage is applied to a sample from the upper side of a reflective film 16. The film 1b may be formed by additionally providing a material having electrical conductivity such as ZnO to a predetermined material.

Figure 9B:
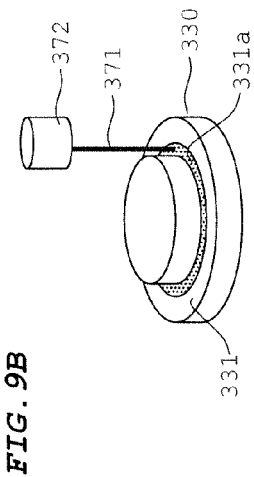
FIGS. 9A to 9E are a perspective view of a fluorescence detection device according to a second embodiment when viewed from the lateral direction, perspective views of the configuration of a clamper, and diagrams of the state of red blood cells.
Figure 9C:
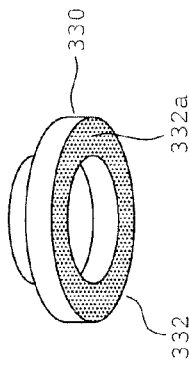
Figure 9A:
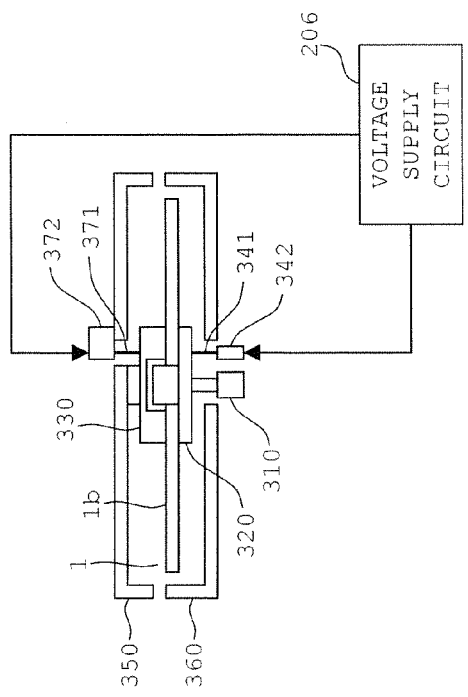

FIG. 9A is a perspective view of a fluorescence detection device 100 according to the embodiment when viewed from the lateral direction, and FIGS. 9B and 9C are perspective views of the configuration of a clamper 330.

In the embodiment, as illustrated in FIG. 9A, the electrode 351 is omitted from the first embodiment described above, and an electrical conducting part 371 and a support part 342 that supports the electrical conducting part 371 are disposed on the upper side of an upper casing 350. Moreover, as illustrated in FIGS. 9B and 9C, electrodes 331a and 332a in an annular shape are disposed on a top face 331 and an under face 332 of the clamper 330, respectively. The electrical conducting part 371 is formed of an electrically conductive member having elasticity, and biased from the upper side by a support part 372 as the electrical conducting part 371 is contacted with the electrode 331a. A voltage is supplied to the electrical conducting part 371 from a voltage supply circuit 206 through the support part 372. The electrodes 331a and 332a are electrically connected to each other in the interior of the clamper 330.

In the fluorescence detection device 100 thus configured, when a biosensor substrate 1 is set on a turntable 320 and the upper casing 350 is closed, the electrode 332a disposed on the under face 332 of the clamper 330 is contacted with the inner radial portion of the film 1b, Thus, a voltage can be applied to the film 1b through the electrical conducting part 371 and the electrodes 331a and 332a.

Figure 9E:
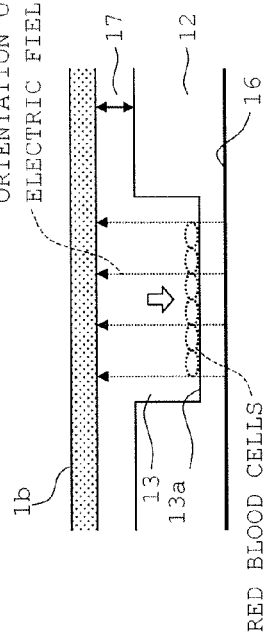
Figure 9D:
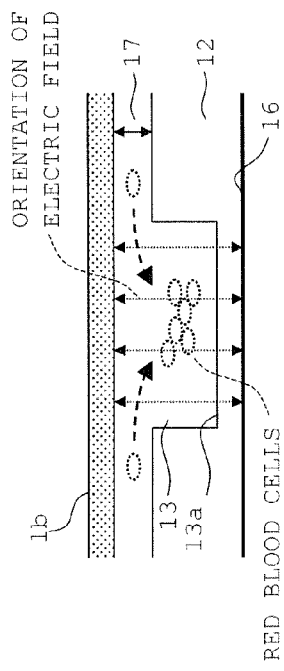

In this manner, in S18 in FIG. 8A, when an alternating voltage in an anti-phase to the phase of the alternating voltage applied to the reflective film 16 is applied to the film 1b, red blood cells remaining in the gap 17 are gathered on the wells 13, and aggregated in the wells 13 as illustrated in FIG. 9D. Moreover, in S21 in FIG. 8A, when a negative voltage opposite to the reflective film 16 is applied to the film 1b, the red blood cells are attracted to a bottom face portion 13a, and uniformly arranged on the bottom face portion 13a as illustrated in FIG. 9E.

<Effect of Second Embodiment>

According to the embodiment, instead of the electrode 351 in the first embodiment described above, a voltage is applied to the red blood cells from the upper side of the reflective film 16 through the film 1b as illustrated in FIGS. 9D and 9E. Thus, the orientation of the electric field can be accurately directed to upward and downward directions as compared with the first embodiment described above, and the magnitude of the electric field can be accurately set, so that it is possible that the red blood cells are surely aggregated and red blood cells are surely arranged on the bottom face portion 13a.

<Third Embodiment>

In the first embodiment described above, a single reflective film 16 is provided on the entire region of the biosensor substrate 1. However, in this embodiment, different reflective films 23 and 25 respectively corresponding to regions A1 and A2 are provided.

FIGS. 10A to 10H are diagrams of a fabrication method for a biosensor substrate 1 according to the embodiment.

Figures 10A, 10B, 10C, 10D, 10E, 10F, 10G, 10H:
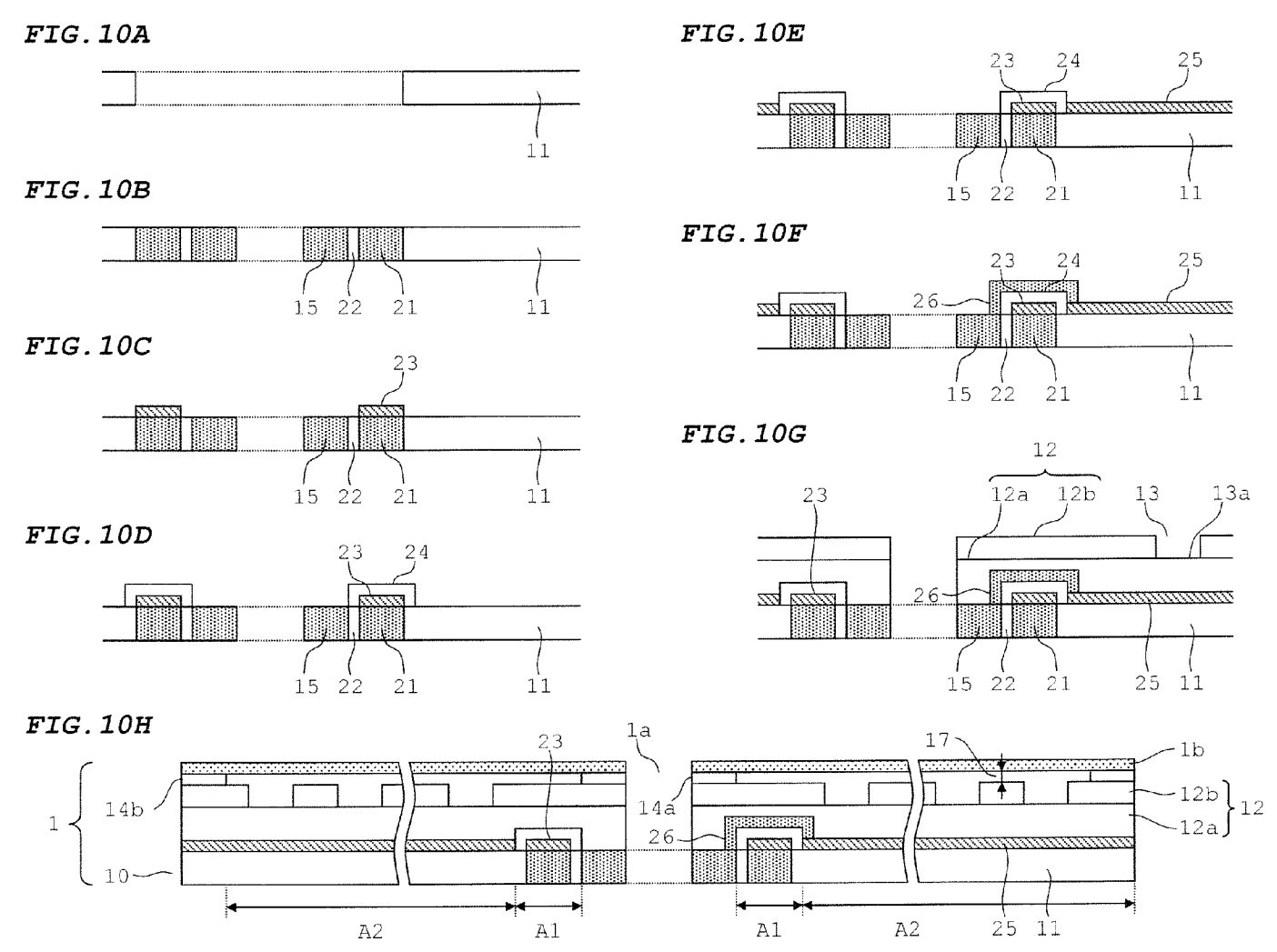

First, as illustrated in FIG. 10A, a base substrate 11 is formed by injection molding. A series of tracks is formed on the top face of the base substrate 11. Subsequently, as illustrated in FIG. 10B, a conductive ring 21 in an annular shape, an insulating ring 22, and a conductive ring 15 similar to the first embodiment described above are attached to a hole formed in the center of the base substrate 11 in this order. In this case, the conductive rings 21 and 15 are not electrically connected to each other by the insulating ring 22.

Subsequently, as illustrated in FIG. 10C, a reflective film 23 formed of a material (ZnO) similar to the reflective film 16 in the first embodiment described above is formed on the top face of the conductive ring 21. Thus, the reflective film 23 and the conductive ring 21 are in an electrically connected state. Subsequently, as illustrated in FIG. 10D, an insulating film 24 is formed to cover the top face of the reflective film 23. Subsequently, as illustrated in FIG. 10E, the reflective film 25 is formed on the top face of the base substrate 11. At this time, the reflective films 23 and 25 are not electrically connected to each other through the insulating film 24.

Subsequently, as illustrated in FIG. 10F, an electrical conducting part 26 is disposed through the top face of the insulating film 24 in such a manner that one point on the top face of the conductive ring 21 in the circumferential direction is connected to one point on the top face of the reflective film 25 in the circumferential direction. The electrical conducting part 26 includes a material having electrical conductivity, and is formed in which for example, silver paste generated by mixing silver particles with a resin and the like is disposed as illustrated in FIG. 10F. Thus, the reflective film 25 and the conductive ring 15 are in an electrically connected state. Subsequently, as illustrated in FIG. 10G, a bottom face layer 12a and a top face layer 12b are disposed on the top faces of the members in the state illustrated in FIG. 10F, similarly to the first embodiment described above. It is noted that although the thicknesses of the insulating film 24 and the electrical conducting part 26 are actually very thin, the thickness of the bottom face layer 12a is depicted thick in FIG. 10G for convenience.

Subsequently, as illustrated in FIG. 10H, an accommodating body 10 is completed by disposing the shelf portions 14a and 14b, and the biosensor substrate 1 is completed by attaching the film 1b to the accommodating body 10, similarly to the first embodiment described above.

Figure 11B:
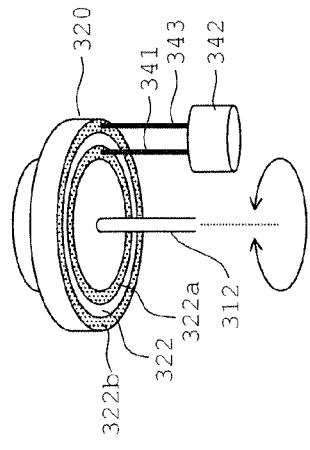
FIGS. 11A to 11D are schematic diagrams of the configuration of a turntable according to the third embodiment, a flowchart of the procedures in performing a fluorescence detection process of a fluorescence detection device, and a diagram of moving red blood cells positioned on an inner radial portion to an outer circumferential direction.
Figure 11A:
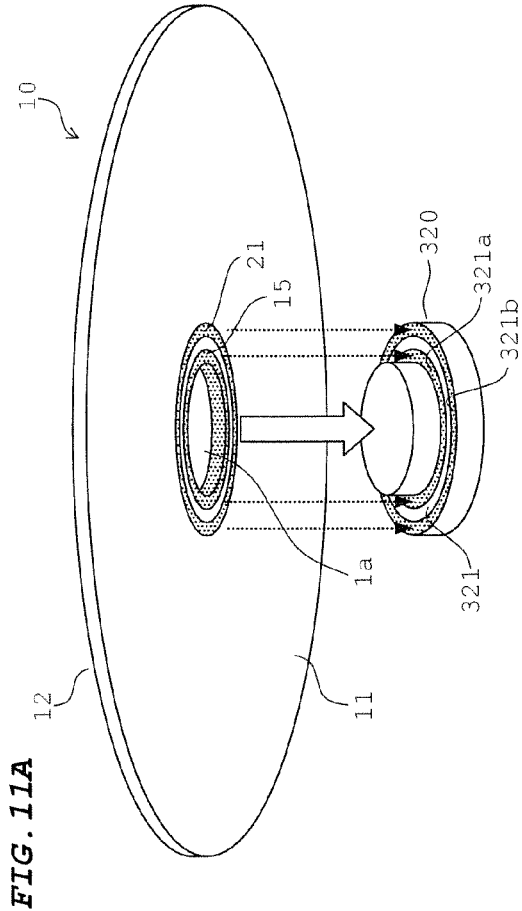

FIGS. 11A and 11B are schematic diagrams of the configuration of a turntable 320 according to the embodiment.

Referring to FIG. 11A, an electrode 321b in an annular shape is disposed on a top face 321 of the turntable 320 at a position opposite to the conductive ring 21 of the biosensor substrate 1. The biosensor substrate 1 is set on the turntable 320, and the conductive rings 15 and 21 of the biosensor substrate 1 are electrically connected to an electrode 321a and the electrode 321b, respectively.

Referring to FIG. 11B, an electrode 322b in an annular shape is disposed outside an electrode 322a on an under face 322 of the turntable 320. The electrodes 321b and 322b are electrically connected to each other in the interior of the turntable 320. Moreover, an electrical conducting part 343 is disposed on a support part 342. The electrical conducting part 343 is formed of an electrically conductive member having elasticity, and biased from the lower side by the support part 342 as the electrical conducting part 343 is contacted with the electrode 322b. A voltage is supplied from the voltage supply circuit 206 to the electrical conducting part 343 through the support part 342.

When the turntable 320 is thus configured, the voltage supplied to the electrical conducting part 343 is supplied to the conductive ring 21 through the electrodes 321b and 322b even in the case where the turntable 320 is rotated by the spindle 312. Thus, a voltage is supplied to the reflective film 23 electrically connected to the conductive ring 21.

Figure 11D:
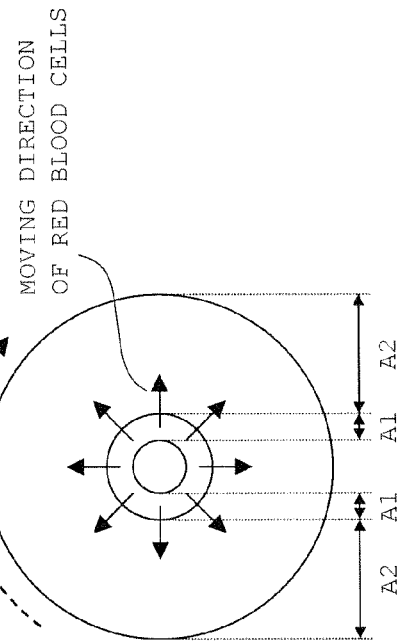
Figure 11C:
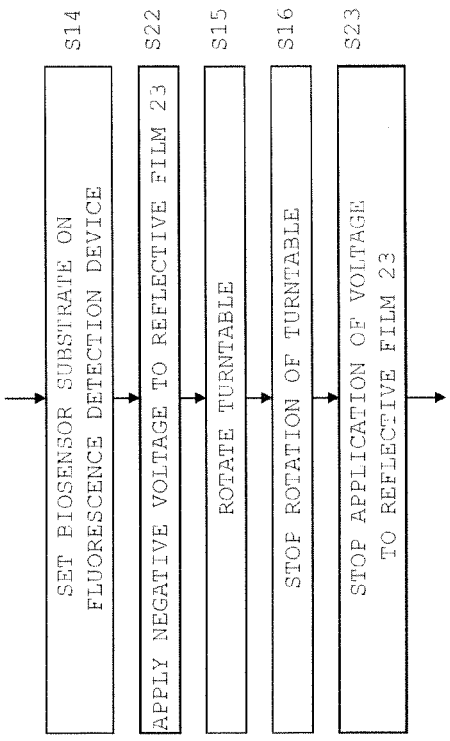

FIG. 11C is a flowchart of the procedures in performing a fluorescence detection process of a fluorescence detection device 100 according to the embodiment. It is noted that FIG. 11C shows portions different from the procedures of the first embodiment described above illustrated in FIG. 8A, and a voltage is applied to the reflective film 25 in S17 and S20 in FIG. 8A similarly to the application of a voltage to the reflective film 16 in the first embodiment described above.

When the user sets the biosensor substrate 1 on the fluorescence detection device 100 (S14) and the operation of preparing fluorescence detection of the fluorescence detection device 100 is started, a controller 205 applies a negative voltage to the reflective film 23 (S22). At this time, as illustrated in FIG. 11D, since red blood cells positioned on the region A1 are negatively charged, a negative voltage is applied to the reflective film 23 below the region A1 of the well layer 12, and the red blood cells are difficult to remain on the region A1 of the well layer 12. When the turntable 320 is rotated as illustrated in FIG. 11D (S15) and centrifugal force is applied to the red blood cells positioned on the inner radial portion in this state, the red blood cells positioned on the inner radial portion are easily moved in the outer circumferential direction as compared with the first embodiment described above.

In this manner, after a lapse of a predetermined time period, the controller 205 stops the rotation of the turntable 320 (S16), and stops the application of the voltage to the reflective film 23 (S23).

<Effect of Third Embodiment>

According to the embodiment, the fluorescence detection device 100 is configured in which the reflective films 23 and 25 respectively corresponding to the regions A1 and A2 of the well layer 12 are disposed, and a voltage is separately applied to the reflective films 23 and 25. Moreover, a negative voltage is applied to the reflective film 23 when the biosensor substrate 1 is rotated and red blood cells positioned at the inner radial portion are moved in the outer circumferential direction, so that the red blood cells positioned on the inner radial portion can be easily moved in the outer circumferential direction as compared with the first embodiment described above.

<Fourth Embodiment>

Figure 12A:
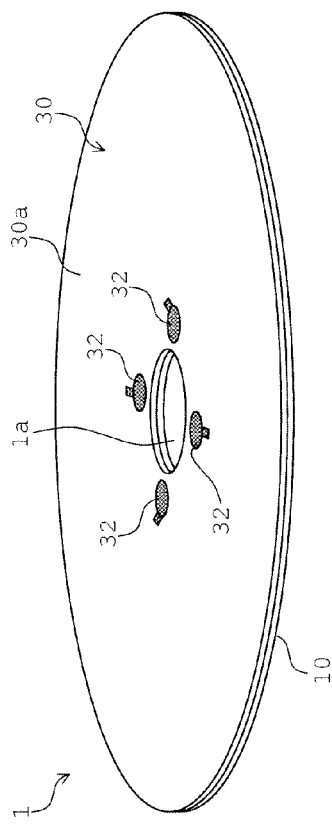
FIGS. 12A to 12C are schematic diagrams of the configuration of a biosensor substrate according to a fourth embodiment.
Figure 12B:
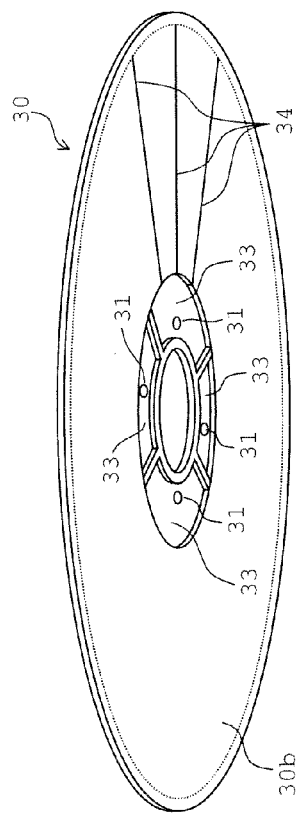
Figure 12C:
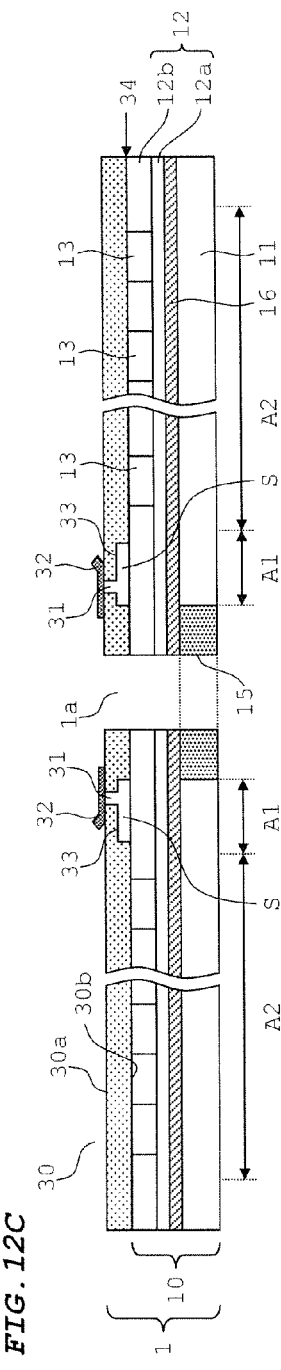

In the first embodiment described above, the film 1b is disposed on the top face of the accommodating body 10. However, in this embodiment, a cover 30 is fixed to an accommodating body 10 instead of the film 1b, FIGS. 12A to 12C are schematic diagrams of the configuration of a biosensor substrate 1 according to the embodiment. FIG. 12A is a diagram in the case where the biosensor substrate 1 is viewed from the upper side, FIG. 12B is a diagram of the configuration of an under face 30b of the cover 30, and FIG. 12C is a cross sectional view of the biosensor substrate 1.

Referring to FIGS. 12A and 12E, four holes 31 are formed on the inner radial portion of the cover 30 so as to penetrate through the cover 30 in the vertical direction, and four covers 32 are disposed to stem these four holes 31 on a top face 30a of the cover 30. A removable and reattachable adhesive is applied in advance on the under face of the cover 32, and the user can easily remove the cover 32 from the top face 30a, and can again dispose the cover 32, which has been removed from the top face 30a, on the top face 30a.

Referring to FIG. 12B, four recesses 33 are formed on the inner radial portion of the under face 30b of the cover 30 in such a manner that the lower ends of these four holes 31 are included. Moreover, a plurality of passages 34 radially extended is formed on the outer radial portion of the under face 30b across the entire region in the circumferential direction. It is noted that in FIG. 12B, only a part of the passages 34 is depicted for convenience.

Referring to FIG. 12C, when the user uses the biosensor substrate 1, first, the user peels the cover 32 off from the top face 30a, and drops a sample which is prepared by applying fluorescence labeling to a test sample (red blood cells) in advance, onto a space S formed of the recess 33 and the region A1 of a well layer 12 through the holes 31. The user then again attaches the removed cover 32 at the original position on the top face 30a. After that, the user sets the biosensor substrate 1 on the fluorescence detection device 100, and rotates the biosensor substrate 1. Thus, the sample accommodated in the space S is passed through the passages 34 and moved in the outer circumferential direction by centrifugal force, and accommodated in wells 13. The rotation of the biosensor substrate 1 is then stopped, and the processes after S17 in FIG. 8A are performed similarly to the first embodiment described above.

<Effect of Fourth Embodiment>

According to the embodiment, it is sufficient that the cover 32 is peeled and again attached to the original position when the sample is dropped, so that the operation of dropping the sample can be easily performed as compared with the case where the film 1b covering the entire accommodating body 10 is peeled and again attached to the original position as in the first embodiment described above. Moreover, the cover 30 is fixed to the accommodating body 10, so that it is possible to surely prevent the sample from being scattered to the outside.

Furthermore, according to the embodiment, since the four holes 31 and the four recesses 33 are formed on the cover 30, the space S is divided into four portions. Thus, samples based on red blood cells taken from different patients can be accommodated in these four spaces S, so that tests for four patients can be conducted on a single biosensor substrate 1 at the same time. Therefore, the consumption of the biosensor substrate 1 can be suppressed, so that an environmental load and the like can be decreased.

As described above, the embodiments of the present are described. However, the present invention is not limited to the foregoing embodiments at all, and the embodiments of the present can be modified variously other than ones described above.

For example, in the foregoing embodiments, red blood cells are accommodated in the wells 13, and it is determined whether the red blood cells are infected with malaria parasites. A sample to be accommodated in the wells 13 and an item to be a determination target are not limited to them. It may be fine that a sample is one that is negatively or positively charged. Moreover, it may be fine that a sample is charged with static electricity, for example. It is noted that in the case where a sample and an item to be a determination target are positively charged, a voltage of a polarity opposite to the polarity described in the foregoing embodiments is applied to the electrodes according to the foregoing embodiments.

For example, it may be fine that a cell expressing a certain gene or a cell including a greater amount or a shorter amount of a living substance such as a nucleic acid, protein, lipid, and sugar than in a normal amount is detected as a certain cell from various cell groups. This certain cell may be cells exit in the natural world, or cells artificially processed. Although cells exiting in the natural world are not limited more specifically, the cells include, for example, a pathogenic cell, lesion cell, cell infected with a pathogenic bacteria or pathogenic organism, mutant cell, unknown cell including a specific nature, and the like. Moreover, although artificial processes are not limited more specifically, the processes include, for example, a physical process (for instance, electromagnetic wave application), chemical process (for instance, drug treatment), genetic engineering process (for instance, genetic modification processing), and the like.

Furthermore, it may be fine that in these artificial processes, a process whose influence on cells is known is applied to a cell group and a cell that does not exhibit the influence or a cell that strongly exhibits the influence is detected as a certain cell. For example, a cell resistant to or highly sensitive to drug treatment can be detected as a certain cell.

In addition, the types of cell groups are not limited more specifically as well. The cell groups may be groups of cells derived from multicellular organisms in addition to groups of unicellular organisms. Cells derived from a multicellular organism include, for example, a cell obtained from normal tissue or pathological tissue of an organism, a cultured cell derived from these cells, and the like. Moreover, organisms from which these cells are obtained are not limited more specifically. For example, cells may be cells derived from animals, or cells derived from plants. More specifically, detection target cells include, for example, cells derived from vertebrate animals (more specifically mammals and birds), cells derived from insects, plant cultured cells, and the like. However, a detection target cell is not limited to these cells. Furthermore, cell groups may be groups of the same cells or may be groups including a plurality of types of cells.

Furthermore, in the foregoing embodiments, the shape of the well 13 is set in a cylindrical shape as illustrated in FIGS. 1A and 2A, but not limited to this shape. The shape of the well 13 may be set in a shape other than a cylindrical shape such as a quadrangular prism, elliptic cylinder, cone, and pyramid as long as a sample can be accommodated. The values of d1 to d6 are not limited to the values in the foregoing embodiments, and values may be appropriately set. Furthermore, the address length on the reflection plane R may be one that the position of the well 13 can be identified, and various setting methods can be used.

In addition, in the foregoing embodiments, the wavelength of the excitation light emitted from the semiconductor laser 101 is set to 405 nm. However, the wavelength is not limited to this wavelength, and the wavelength may be appropriately set depending on types of fluorescence labeling used for a sample to be a measurement target. Various parameters of the optical system such as the transmission wavelength ranges of the dichroic prism 105 and the filter 111 are appropriately changed in accordance with changes in the wavelengths of the excitation light and fluorescence. Moreover, in the foregoing embodiments, the NA of the excitation light is set to 0.34. However, the NA is not limited to this NA, and the NA may be appropriately set depending on the size of a sample to be a measurement target. It is noted that since the NA of the objective lens 107 is increased to raise a detection light quantity, a greater NA is desirable to the objective lens 107.

Furthermore, in the foregoing embodiments, the track is formed of a groove. However, address information may be formed of pit strings like existing CDs, or address information may be formed of a combination of a pit string and a groove.

In addition, in the first embodiment described above, as illustrated in FIGS. 3A to 3F, the base substrate 11 is formed by injection molding, and the bottom face layer 12a, the top face layer 12b, and the shelf portions 14a and 14b formed in advance are disposed on the top face of the reflective film 16. However, the fabrication method for the biosensor substrate 1 is not limed to this method, and the biosensor substrate 1 may be fabricated by other methods appropriately. For example, the bottom face layer 12a may be stacked by spin coating, and the top face layer 12b and the shelf portions 14a and 14b may be formed by photo-polymerization molding. Moreover, the bottom face layer 12a, the top face layer 12b, and the shelf portions 14a and 14b may be separately formed by stampers and bonded to one another.

Furthermore, in the first embodiment described above, electricity is conducted between the reflective film 16 and the under face side of the base substrate 11 through the conductive ring 15, and in the third embodiment described above, electricity is conducted between the reflective films 23 and 25 and the under face side of the base substrate 11 through the conductive rings 21 and 15, respectively. However, the configurations are not limited to these configurations, and electricity may be conducted between the reflective film and the under face side of the base substrate 11 by different methods appropriately. It maybe fine that for example, a hole is opened on the base substrate 11, silver paste generated by mixing silver particles with a resin and the like is poured into the hole, the silver paste is hardened, and the reflective film on the top face side is electrically connected to the electrode disposed on the under face side.

In addition, in the foregoing embodiments, the velocity and time to rotate the biosensor substrate 1 in S15 in FIG. 8A, the voltage value and time of the alternating voltage applied in S17 and S18, the voltage value applied in S20 and S21, and the like may be held on the track portion corresponding to the region A1 of the biosensor substrate 1. The operation of fluorescence detection may be performed based on these read items of information. In the foregoing embodiments, since the wells 13 are not formed on the region A1 of the well layer 12 and it is difficult to enter unnecessary reflected light caused by the wells 13 to the photodetector 109 when these items of information are read, it is possible to highly accurately acquire these items of information.

Furthermore, in the foregoing embodiments, the shape of the biosensor substrate 1 is in a disk shape. However, the shape is not limited to this shape, and the biosensor substrate 1 may have the outline is in a square shape.

In addition, in the foregoing embodiments, a positive voltage is applied to the reflective films 16 and 25 corresponding to the region A2. However, the voltage application is not limited to this method, and the biosensor substrate 1 may be configured in which a positive voltage is applied to only the lower side of the region on which the wells 13 are positioned.

Moreover, in the foregoing embodiments, the film 1b or the cover 30 is disposed so as to cover the top face side of the accommodating body 10. However, the biosensor substrate 1 may have such a configuration in which neither the film 1b, nor the cover 30 is provided, that is, the top face of the accommodating body 10 is not covered with a member such as the film 1b and the cover 30. In this case, a sample is directly dropped onto the wells 13, and the processes after S17 in FIG. 8A are performed. Thus, similarly to the foregoing embodiments, red blood cells can be uniformly arranged on the bottom face portions 13a of the wells 13.

Furthermore, in the foregoing embodiments, a sample is applied with fluorescence labeling, and then the sample is dropped onto the biosensor substrate 1. However, the method is not limited to this method, and it may be fine that a fluorescent material dyestuff and a sample are separately dropped onto the biosensor substrate 1, and a process of applying fluorescence labeling to the sample is performed on the biosensor substrate 1.

In addition, in the foregoing embodiments, a voltage is directly supplied to the reflective films 16, 23, and 25 and the film 1b through the electrode. However, the method is not limited to this method, and a voltage may be indirectly supplied by an electromagnetic induction method.

Moreover, in the third embodiment described above, similarly to the first embodiment described above, the electrode 351 is disposed on the under face of the upper casing 350. However, the configuration is not limited to this configuration, and it may be fine that the electrode 351 is divided into two electrodes so as to correspond to the regions A1 and A2 and voltages are separately applicable. In this case, voltages different from voltages applied to the reflective films 23 and 25 located below the electrodes are applied to two electrodes.

Furthermore, the film 1b in the third embodiment described above is used for preventing a sample from being scattered similarly to the first embodiment described above. However, similarly to the second embodiment described above, a voltage may be applied to red blood cells from the upper side of the reflective films 23 and 25 through the film 1b. In addition, in this case, the film 1b may be configured in which voltages of different polarities are applied to the regions corresponding to the regions A1 and A2 of the film 1b.

Moreover, an electrode may be provided on the cover 30 in the fourth embodiment described above so as to correspond to the reflective film. The electrode in this case is disposed on the interior of the cover 30, and a voltage is supplied from the inner radial portion as in FIG. 9A.

Furthermore, in the foregoing embodiments, the materials of the reflective films 16, 23, and 25 are formed of ZnO. However, the materials are not limited to ZnO, and the reflective films 16, 23, and 25 maybe formed of other materials having electrical conductivity and reflectance similar to these of ZnO. For example, the reflective films 16, 23, and 25 may be formed of $SnO_2$, $in_2O_3$, $\beta Ga_2O_3$, $TeO_2$, $GeO_2$, $WO_3$, and $MoO_3$, and maybe formed of a composite material obtained by doping these materials as base materials with A1, Bi, Cr, or the like. In addition, the reflective films 16, 23, and 25 may be formed of a multi-layer film of these materials in order to improve reflectance or thermal conductivity.

Moreover, the reflective films 16, 23, and 25 may be formed of a conductive heat generating material such as nichrome (Ni—Cr alloy), chromium, tungsten, molybdenum, and manganese. The conductive heat generating material is a material of high heat generating properties when an electric current is carried. The electric resistivity of the conductive heat generating material is desirably 30 n Ω·m or greater. Furthermore, the electric resistivity of the conductive heat generating material is more desirably 50 n Ω·m or greater in consideration of heat transfer efficiency, for example.

As described above, when the reflective films 16, 23, and 25 are formed of a conductive heat generating material, a sample can be warmed near the sample, and temperature can be efficiently managed in the case where the sample is measured by a measuring method that needs temperature management. Examples of measurement that needs temperature management include DNA detection using a PCR method.

Moreover, the base substrate 11 is formed of polycarbonate. However, the material is not limited to polycarbonate, and such a material maybe fine that excitation light and fluorescence are transmitted. The base substrate 11 may be formed of a translucent material such as polymethylmethacrylate, amorphous polyolefin, and a biodegradable material. Furthermore, the well layer 12 is formed of PDMS. However, the material is not limited to PDMS, and the well layer 12 may be formed of an ultraviolet curing resin, silicone, polycarbonate, polymethylmethacrylate, amorphous polyolefin, and the like.

In addition to this, the embodiment of the present invention can be appropriately and variously modified within the scope of the technical ideas described in claims.

Moreover, the terms "upper" and "lower" in claims and the specification in the present application are definitions in order to clarify the positional relationship between the components for convenience, and are not necessarily interpreted in a limited manner as the terms mean upper and lower with respect to the ground.

What is claimed is:

1. A sample-holding carrier comprising:
   a substrate to which-irradiation light is entered from an under face, the substrate having a hole at its center;
   a track formed on a top face of the substrate;
   a first reflective film disposed on the track and having electrical conductivity, the first reflective film extending over the hole of the substrate to cover a part of the hole;
   a sample accommodating portion disposed above the first reflective film and having a bottom portion; and
   a first current carrying part disposed in the hole of the substrate and under the first reflective film to electrically contact the first reflective film, the first current carrying part being configured to apply an externally applied voltage to the first reflective film.

2. The sample-holding carrier according to claim 1, further comprising:
   a second reflective film disposed on a region on which the sample accommodating portion is not disposed and having electrical conductivity; and
   a second current carrying part contacting the second reflective film, the second current carrying part being configured to apply an externally applied voltage to the second reflective film,
   wherein the second reflective film is separate and insulated from the first reflective film on the top face of the substrate.

3. The sample-holding carrier according to claim 2, further comprising an insulating film disposed on the second reflective film, wherein
   the first current carrying part is disposed on the insulating film.

4. The sample-holding carrier according to claim 2, further comprising:
   an insulating film disposed on the second reflective film, wherein
   the first current carrying part is disposed on the insulating film.

5. The sample-holding carrier according to claim 1, comprising a cover part that covers a top face of the sample-holding carrier,
   wherein the cover part has electrical conductivity, and is configured such that a voltage is applicable to the cover part from an outside.

6. The sample-holding carrier according to claim 1, wherein the first reflective film is formed of a conductive heat generating material.

7. The sample-holding carrier according to claim 1, wherein the first reflective film is applied with electric charges of a polarity opposite to a polarity of electric charges stored in a sample accommodated in the sample accommodating portion.

8. The sample-holding carrier according to claim 1, wherein a plurality of the sample accommodating portions is disposed above the first reflective film.

9. The sample-holding carrier according to claim 1, wherein the first current carrying part is in direct contact with the first reflective film to apply the externally applied voltage to the first reflective film.

10. The sample-holding carrier according to claim 1, wherein the first current carrying part is a ring-shaped conductor.

11. A fluorescence detection device that irradiate a sample-holding carrier holding a sample applied with fluorescence labeling with irradiation light and detects fluorescence emitted from the sample by irradiating the sample-holding carrier with the irradiation light, wherein:
the sample-holding carrier includes:
a substrate to which irradiation light is entered from an under face, the substrate having a hole at its center;
a track formed on a top face of the substrate;
a first reflective film disposed on the track and having electrical conductivity, the first reflective film extending over the hole of the substrate to cover a part of the hole;
a sample accommodating portion disposed above the first reflective film and having a bottom portion; and
a first current carrying part disposed in the hole of the substrate and under the first reflective film to electrically contact the first reflective film, the first current carrying part being configured to apply an externally applied voltage to the first reflective film; and
the fluorescence detection device includes:
a light source configured to emit the irradiation light;
an objective lens configured to converge the irradiation light on the sample-holding carrier;
a photodetector configured to receive the irradiation light reflected by the first reflective film;
a fluorescence detector configured to receive fluorescence emitted from the sample by irradiating the sample-holding carrier with the irradiation light; and
a voltage applying unit configured to apply a voltage to the first reflective film through the first current carrying part.

12. The fluorescence detection device according to claim 11, wherein:
the sample-holding carrier further includes:
a second reflective film disposed on a region on which the sample accommodating portion is not disposed and having electrical conductivity; and
a second current carrying part contacting the second reflective film configured to apply an externally applied voltage to the second reflective film; and
the voltage applying unit individually applies a voltage to the first reflective film and the second reflective film through the first current carrying part and the second current carrying part.

13. The fluorescence detection device according to claim 12, further comprising an insulating film disposed on the second reflective film,
wherein the first current carrying part is disposed on the insulating film.

14. The fluorescence detection device according to claim 12, further comprising:
an insulating film disposed on the second reflective film, wherein
the first current carrying part is disposed on the insulating film.

15. The fluorescence detection device according to claim 11, wherein the voltage applying unit includes an electrode disposed on a top face side of the sample-holding carrier and opposite to a region on which the sample accommodating portion is disposed.

16. The fluorescence detection device according to claim 11, wherein the first current carrying part is in direct contact with the first reflective film to apply the externally applied voltage to the first reflective film.

17. A sample-holding carrier comprising:
a substrate to which irradiation light is entered from an under face, the substrate having a hole at its center;
a track formed on a top face of the substrate;
a first reflective film disposed on the track and having electrical conductivity;
a sample accommodating portion disposed above the first reflective film and having a bottom portion; and
a first current carrying part contacting the first reflective film, the first current carrying part being configured to apply an externally applied voltage to the first reflective film;
a second reflective film disposed on a region on which the sample accommodating portion is not disposed and having electrical conductivity;
a second current carrying part contacting the second reflective film configured to apply an externally applied voltage to the second reflective film;
a conductive ring disclosed in the hole of the substrate; and
an insulating film disposed on the second reflective film,
wherein the second reflective film is separate and insulated from the first reflective film on the top face of the substrate
the conductive ring, the second reflective film and the first reflective film are disposed on the top face of the substrate in this order,
the first current carrying part is disposed on the insulating film, and
the conductive ring connects to the first reflective film via the first current carrying part.

* * * * *